United States Patent
Zuo et al.

(10) Patent No.: US 11,744,896 B2
(45) Date of Patent: Sep. 5, 2023

(54) COMPOSITIONS, USE, AND METHOD FOR CDK2-PROTACS FOR CANCER THERAPY AND HEARING LOSS

(71) Applicants: Creighton University, Omaha, NE (US); ST. JUDE CHILDREN'S RESEARCH HOSPITAL, INC. (Tennessee not for profit corporation), Memphis, TN (US)

(72) Inventors: Jian Zuo, Omaha, NE (US); Santanu Hati, Omaha, NE (US); Marisa Laura Zallocchi, Omaha, NE (US); Robert Hazlitt, Boulder, CO (US); Jaeki Min, Memphis, TN (US)

(73) Assignees: CREIGHTON UNIVERSITY, Omaha, NE (US); ST. JUDE CHILDREN'S RESEARCH HOSPITAL, INC. (TENNESSEE NOT FOR PROFIT CORPORATION), Memphis, TN (US)

( * ) Notice: Subject to any disclaimer, the term of this patent is extended or adjusted under 35 U.S.C. 154(b) by 0 days.

(21) Appl. No.: 17/488,080

(22) Filed: Sep. 28, 2021

(65) Prior Publication Data
US 2022/0096642 A1    Mar. 31, 2022

Related U.S. Application Data

(60) Provisional application No. 63/084,090, filed on Sep. 28, 2020.

(51) Int. Cl.
| | | |
|---|---|---|
| *A61K 47/55* | (2017.01) | |
| *A61P 27/16* | (2006.01) | |
| *A61K 47/54* | (2017.01) | |

(52) U.S. Cl.
CPC ............ *A61K 47/55* (2017.08); *A61K 47/545* (2017.08); *A61P 27/16* (2018.01)

(58) Field of Classification Search
CPC ..................................................... A61K 47/55
See application file for complete search history.

(56) References Cited

PUBLICATIONS

Tinworth, Med. Chem. Commun., 2016, 7, 2206.*
Collins, Biochemical Journal, (2017) 474 1127-1147.*
Hati, S , et al., "AZD5438-PROTAC: A selective CDK2 degrader that protects against cisplatin- and noise-induced hearing loss", European Journal of Medicinal Chemistry 226, 113849, 9 pages (2021).

* cited by examiner

*Primary Examiner* — Nizal S Chandrakumar
(74) *Attorney, Agent, or Firm* — Viksnins Harris Padys Malen LLP

(57) ABSTRACT

Provided are CDK2-PROTAC compounds and pharmaceutical compositions thereof that can be used for specific degradation of the cyclin-dependent kinase 2 (CDK2) protein, for treatment of cancers and other CDK2 related diseases as well as for prevention and treatment of hearing loss.

7 Claims, 15 Drawing Sheets
(11 of 15 Drawing Sheet(s) Filed in Color)

COMPOSITIONS, USE, AND METHOD FOR CDK2-PROTACS FOR CANCER THERAPY AND HEARING LOSS

RELATED APPLICATIONS

This application claims the benefit of U.S. Provisional Application No. 63/084,090, filed Sep. 28, 2020, which is incorporated herein by reference in its entirety.

GOVERNMENT SUPPORT

This invention was made with government support under DC015010, DC015444, and CA021765 from the National Institutes of Health, and made with government support under N0014-18-1-2507 awarded by the Navy/ONR and under RH170030 awarded by the Army/MRMC. The government has certain rights in the invention.

TECHNICAL FIELD

The present disclosure relates to CDK2-PROTACs that can be used for specific degradation of the cyclin-dependent kinase 2 (CDK2) protein, for treatment of cancers and other CDK2 related diseases as well as for prevention and treatment of hearing loss.

BACKGROUND

Hearing loss is a major health problem, affecting 1.57 billion people worldwide and the number is estimated to be 2.45 billion by 2050. Hearing loss can be caused by different insults such as the use of chemotherapeutic agents, antibiotics as well as noise, and aging. The use of the chemotherapeutic agent cisplatin causes permanent high-frequency hearing loss in 40-80% of treated cancer patients. Despite extensive research on the mechanisms of hearing loss, currently, there are no FDA-approved drugs available to prevent acquired or age-related hearing loss. Most of the ongoing pre-clinical or clinical trials are only focused on the use of antioxidants, vitamins, and glutathione metabolism as putative therapeutic compounds to prevent hearing loss. More recently, a phase 3 clinical trial on the usage of sodium thiosulfate (STS) to prevent cisplatin-induced hearing loss in pediatric patients with localized hepatocarcinoma has been completed but it has not yet received FDA approval. Thus, identifying novel therapeutic interventions for acquired hearing loss is an immediate unmet need.

Towards our continuous efforts to find the plausible mechanism of cisplatin-induced ototoxicity, we have identified cyclin-dependent kinase 2 (CDK2) as a potential therapeutic target. Our previous work revealed that the CDK2 inhibitors, AZD5438, AT7519, and AT7519-7, can prevent cisplatin-induced ototoxicity in vivo, with low nanomolar CDK2 inhibitory $IC_{50}$ values. Furthermore, by employing a CDK2 knockout mouse model, we demonstrated that the absence of CDK2 confers resistance to cisplatin- and noise-induced hair cell loss. Moreover, the inhibition or degradation of CDK2 has been the focus of many studies seeking therapies for the treatment of various types of cancers. Studies employing AZD5438-based therapies demonstrated that hair cell loss was reduced in vivo in zebrafish lateral line neuromasts, and when delivered orally to adult FVB mice. However, although AZD5438 treatment is protective, it has also been shown that systemic delivery can induce potential toxicity due to off-target effects, limiting its safety margin in humans.

Targeted protein degradation is an emerging strategy to use small molecules to knock down a specific protein by hijacking the ubiquitin-proteasome degradation system. Proteolysis targeting chimera (PROTAC) is a bifunctional molecule comprised of a ligand for the target protein and a ligand for E3 ligase recruitment, connected by a linker, representing a novel drug discovery approach. After the formation of a ternary complex (targeted protein-ligand for the target protein-ligand for E3 ligase), the target protein is ubiquitinated and degraded by the proteasome. An attractive feature of PROTACs is their catalytic mode of action, as one molecule can perform multiple rounds of target ubiquitination and degradation. Due to this feature of PROTACs, they can function at sub-stoichiometric receptor occupancies. Moreover, PROTACs can add an extra layer of target selectivity, thus providing highly selective degraders with reduced off-target effect. The mounting interest in PROTAC drug discovery is also motivated by the potential to target proteins considered "undruggable" via conventional medicinal chemistry approaches. It has been also observed that pan-CDK inhibitors have better efficacy when developed as PROTACs to degrade a specific CDK protein. Recently, the pan-CDK inhibitors SNS-032 and palbociclib were developed into highly selective CDK9 and CDK6 degraders respectively. AT7519- and TMX-2172-PROTACs have been recently identified as CDK2 degraders, but their selectivity for CDK1, which shares high similarities with CDK2 at the active site, was not examined. This is important since CDK1 is a key component of cell cycle regulation and proliferation, and its inhibition can lead to clinical toxicity. Recently, others reported the discovery of CDK2 selective PROTACs which can degrade CDK2 in acute myeloid leukemia (AML) cells in vitro but no in vivo effects were reported.

SUMMARY

Certain embodiments provide a compound having the structure of Formula (1):

$$X\text{-}L\text{-}E \quad (1)$$

wherein X is a cyclin-dependent kinase 2 binding moiety; L is a linking group selected from: alkylene, (alkylene oxide)$_n$-alkylene, —C(═O)-alkylene, —C(═O)-alkylene-(alkylene oxide)$_n$-alkylene, —(C═O)-alkylene-O-alkylene, alkylene-(heteroaryl)-(alkylene oxide)$_m$-alkylene-C(═O)—, and alkylene-(heteroaryl)-(alkylene oxide)$_m$-alkylene; wherein n and m are each independently an integer between 1 and 10; and E is a ubiquitin ligase binding moiety.

In certain embodiments, X is selected from:
a compound having a structure of Formula (2):

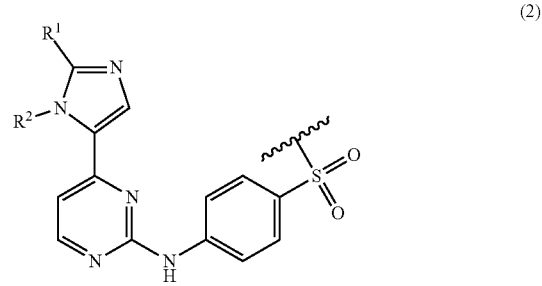

wherein R¹ and R² are each independently H, halo, or $C_{1-6}$ alkyl; and a compound having a structure of Formula (3):

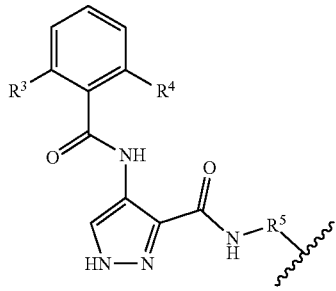

(3)

wherein R³ and R⁴ are each independently H, halo, or $C_{1-6}$ alkyl, and

R⁵ is selected from a 5-10 membered cycloalkyl optionally substituted with 1-5 $R^{5a}$ groups, or a 5-10 membered heterocycloalkyl, wherein $R^{5a}$ is selected from $C_{1-6}$ alkyl or hydroxyl.

In certain embodiments, R¹ and R² are each independently $C_{1-6}$ alkyl.

In certain embodiments, R³ and R⁴ are each independently halo.

In certain embodiments, X is selected from:

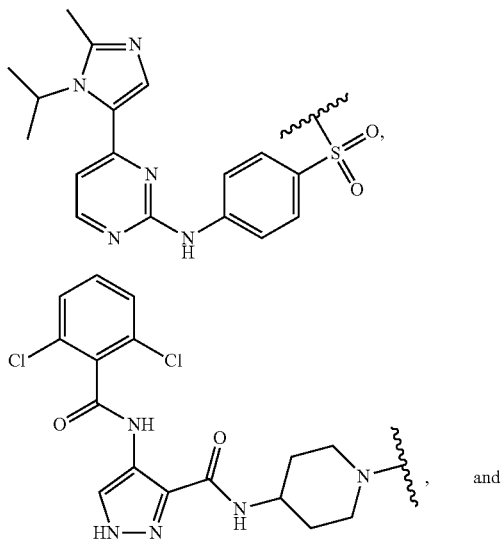

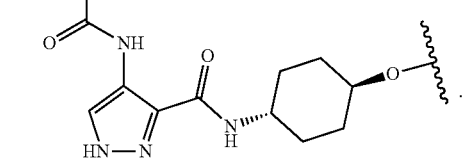

In certain embodiments, X is

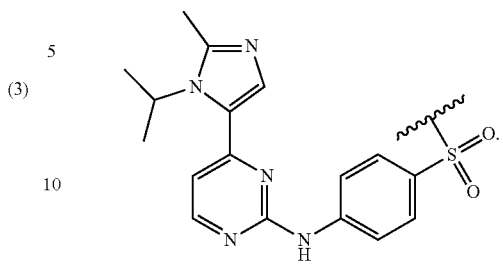

In certain embodiments, L is selected from $C_{1-20}$ alkylene, $(C_{2-3}$ alkylene oxide$)_n$-$C_{2-3}$ alkylene, —C(=O)—$C_{1-20}$ alkylene, —C(=O)—$C_{2-3}$ alkylene-$(C_{2-3}$ alkylene oxide$)_n$-$C_{2-3}$ alkylene, —(C=O)—$C_{1-3}$ alkylene-O—$C_{2-20}$ alkylene, $C_{1-20}$ alkylene-(3-10 membered heteroaryl)-$(C_{2-3}$ alkylene oxide$)_m$-$C_{1-3}$ alkylene-C(=O)—, and $C_{1-20}$ alkylene-(3-10 membered heteroaryl)-$(C_{2-3}$ alkylene oxide$)_m$-$C_{2-3}$ alkylene.

In certain embodiments, L is selected from $C_{1-8}$ alkylene, (ethylene oxide$)_n$-$C_{2-3}$ alkylene, —C(=O)—$C_{1-10}$ alkylene, —C(=O)—$C_{2-3}$ alkylene-(ethylene oxide$)_n$-$C_{2-3}$ alkylene, —(C=O)—$CH_2$—O—$C_{1-10}$ alkylene, $C_{1-10}$ alkylene-(3-7 membered heteroaryl)-(ethylene oxide$)_m$-$CH_2$—C(=O)—, and $C_{1-10}$ alkylene-(3-7 membered heteroaryl)-(ethylene oxide$)_m$-$C_{2-3}$ alkylene.

In certain embodiments, n and m are each independently an integer between 1 and 4.

In certain embodiments, L is selected from

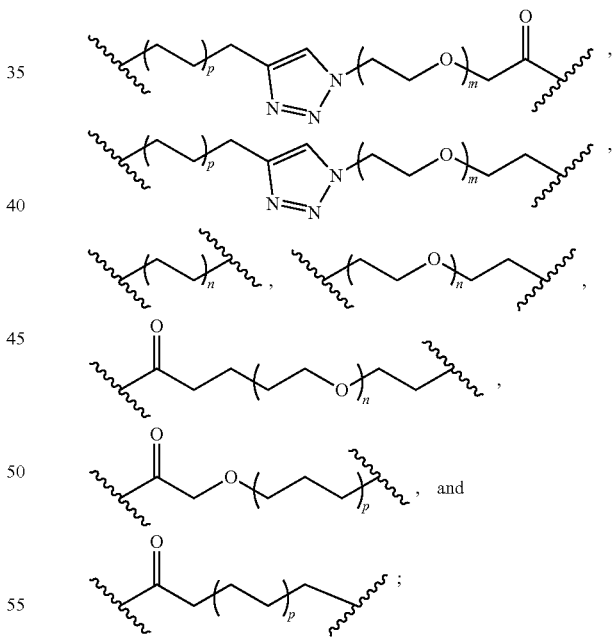

wherein n is an integer between 1 and 4, m is an integer between 2 and 4, and p is an integer between 0 and 4.

In certain embodiments, L is selected from

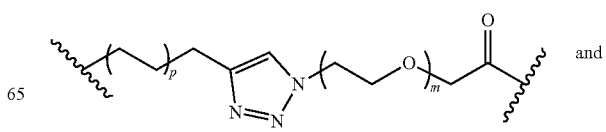

and

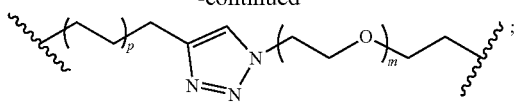

wherein p is 0, 1, 2, or 4, and m is an integer between 2 and 4.

In certain embodiments, E is selected from
a compound having a structure of Formula (4):

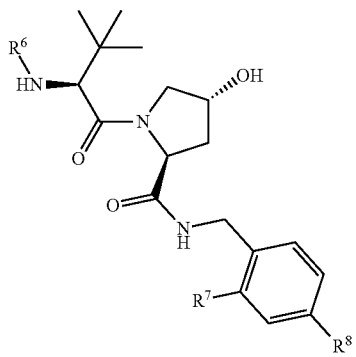

(4)

wherein $R^6$ is selected from a bond linking to L and —C(=O)$R^{6a}$, wherein $R^{6a}$ is selected from H, $C_{1-6}$ alkyl, and $C_{3-6}$ cycloalkyl optionally substituted with 1-3 $R^{6b}$ groups, wherein $R^{6b}$ is selected from $C_{1-6}$ alkyl, halo, and CN;

$R^7$ is selected from H, $C_{1-6}$ alkyl, and —O— linked to L; and $R^8$ is a 3-7 membered heteroaryl optionally substituted with 1-5 $R^{8A}$ substituents, wherein each $R^{8A}$ is independently $C_{1-6}$ alkyl; and a compound having a structure of Formula (5):

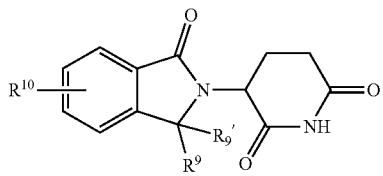

(5)

wherein $R^9$ and $R^{9'}$ are each independently selected from H and $C_{1-6}$ alkyl, or $R^9$ and $R^{9'}$ taken together are oxo; and $R^{10}$ is —NH— linked to L.

In certain embodiments, E is selected from

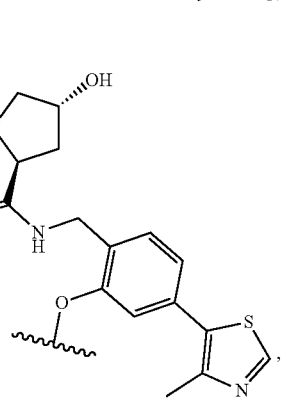

,

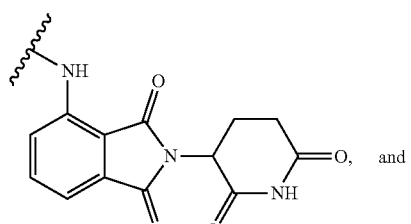

,

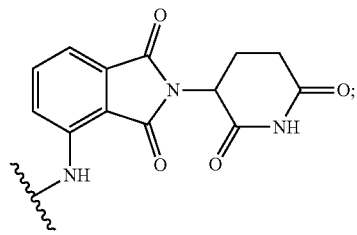

and

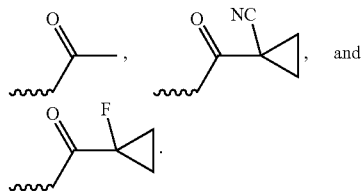

;

wherein $R^8$ is selected from:

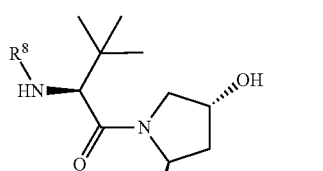

In certain embodiments, the ubiquitin ligase is Cereblon or von Hippel-Lindau.

In certain embodiments, the compound of Formula (1) is:
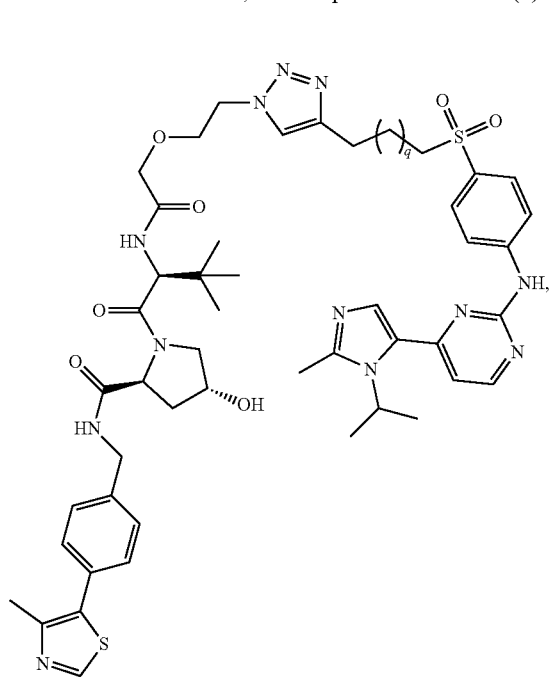
or a pharmaceutically acceptable salt thereof,
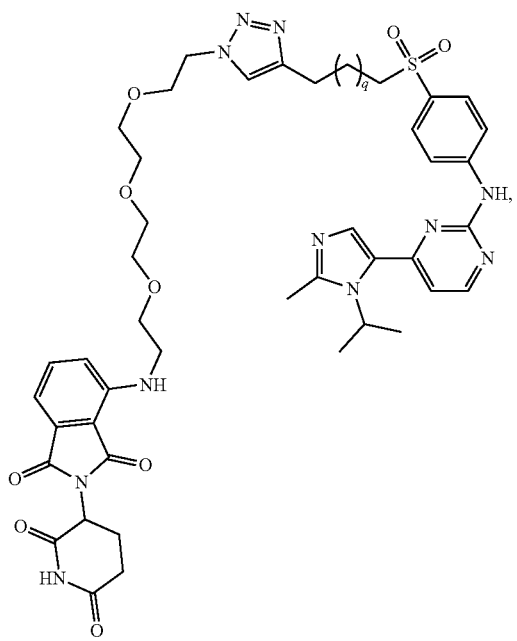
or a pharmaceutically acceptable salt thereof,
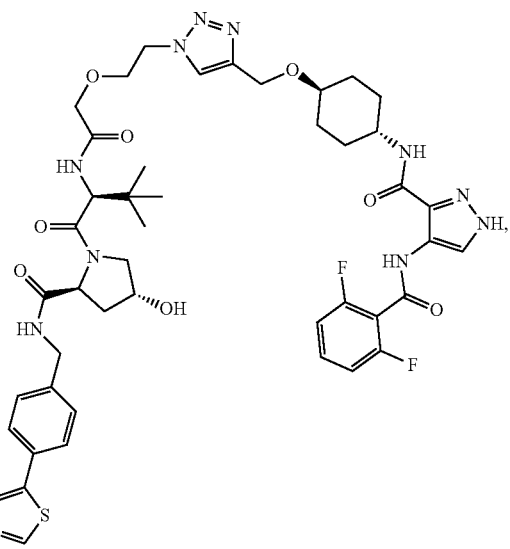
or a pharmaceutically acceptable salt thereof, or
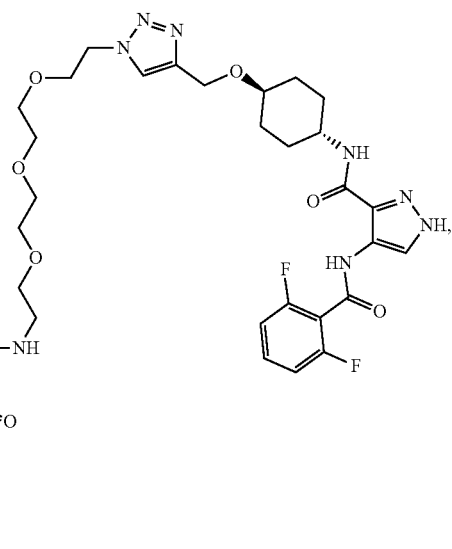
or a pharmaceutical salt thereof,
wherein q is 0 or 1.

In certain embodiments, the compound of Formula (1) is:

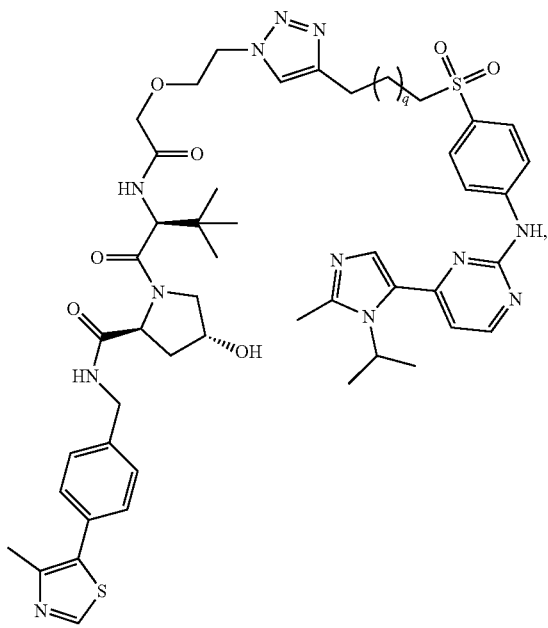

or a pharmaceutically acceptable salt thereof, wherein q is 1.

Certain embodiments provide a pharmaceutical composition comprising a compound having the structure of Formula (1) and a pharmaceutically acceptable carrier.

Certain embodiments provide a method of treating or preventing a disease or disorder in a patient, wherein the disease or disorder is hearing loss, cancer, or a disease associated with cyclin-dependent kinase 2, comprising administering a therapeutically effective amount of a compound of Formula (1).

In certain embodiments, the disease or disorder is hearing loss.

In certain embodiments, the hearing loss is associated with cisplatin treatment, acoustic trauma, use of aminoglycosides, noise, or aging.

In certain embodiments, the hearing loss is associated with cisplatin treatment.

In certain embodiments, the disease or disorder is cancer.

In certain embodiments, the cancer is prostate cancer, colon cancer, breast cancer, ovarian cancer, lung cancer, melanoma, myeloma, glioblastoma, lymphoma, or hepatocellular carcinoma.

In certain embodiments, X of Formula (1) is selected from:

a compound having a structure of Formula (2):

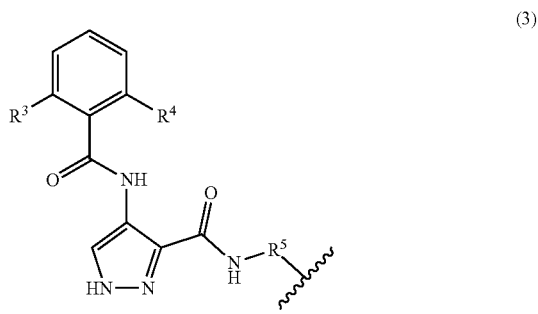

wherein $R^1$ and $R^2$ are each independently H, halo, or $C_{1-6}$ alkyl; and a compound having a structure of Formula (3):

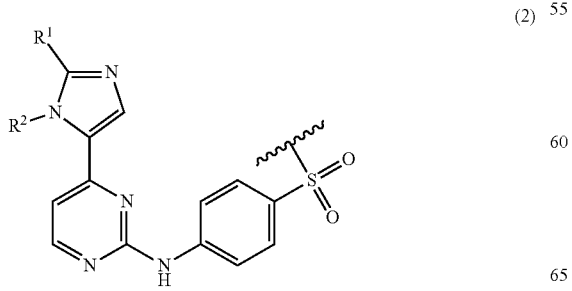

wherein $R^3$ and $R^4$ are each independently H, halo, or $C_{1-6}$ alkyl, and $R^5$ is selected from a 5-10 membered cycloalkyl optionally substituted with 1-5 $R^{5a}$ groups, or a 5-10 membered heterocycloalkyl, wherein $R^{5a}$ is selected from $C_{1-6}$ alkyl or hydroxyl.

In certain embodiments, X of Formula (1) is selected from

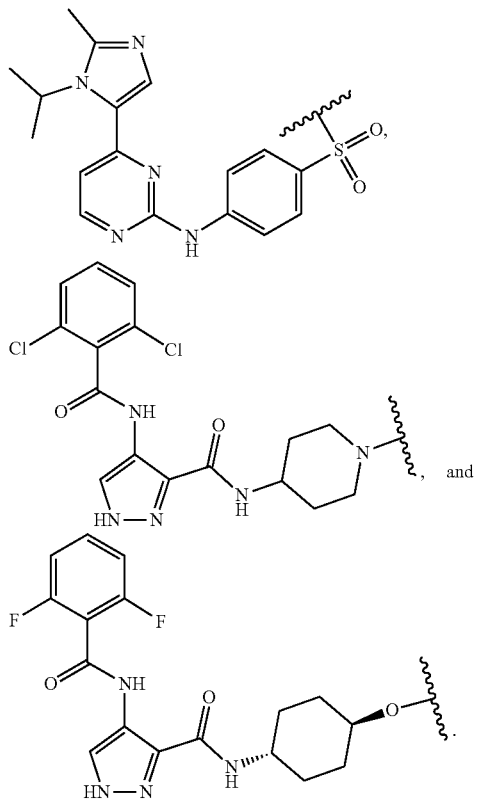

, and

In certain embodiments, L of Formula (1) is selected from

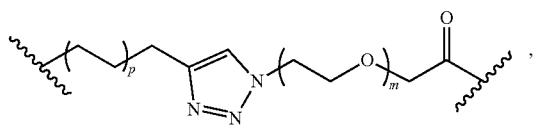

,

-continued

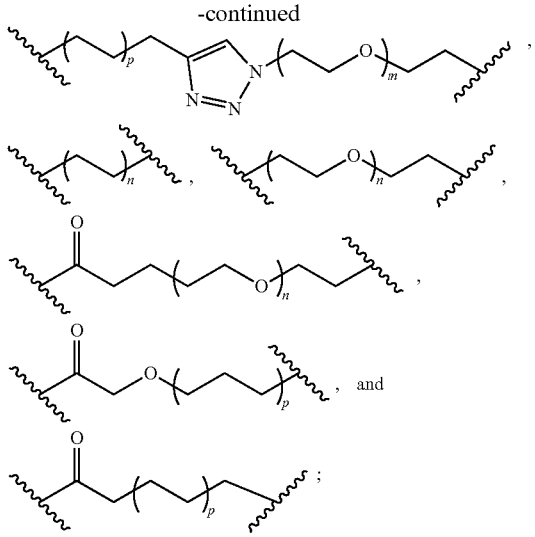

wherein n is an integer between 1 and 4, m is an integer between 2 and 4, and p is an integer between 0 and 4.

In certain embodiments, E of Formula (1) is selected from a compound having a structure of Formula (4):

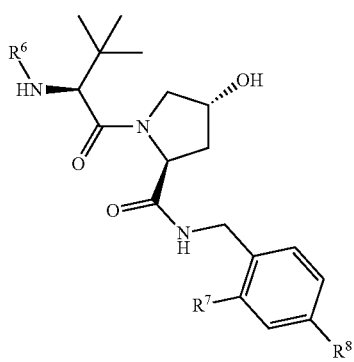

(4)

wherein $R^6$ is selected from L and —C(=O)$R^{6a}$, wherein $R^{6a}$ is selected from H, $C_{1-6}$ alkyl, and $C_{3-6}$ cycloalkyl optionally substituted with 1-3 $R^{6b}$ groups, wherein $R^{6b}$ is selected from $C_{1-6}$ alkyl, halo, and CN;
$R^7$ is selected from H, $C_{1-6}$ alkyl, and —O-L; and
$R^8$ is a 3-7 membered heteroaryl optionally substituted with 1-5 $R^{8A}$ substituents, wherein each $R^{8A}$ is independently $C_{1-6}$ alkyl; and a compound having a structure of Formula (5):

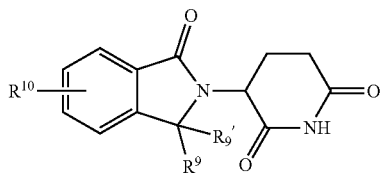

(5)

wherein $R^9$ and $R^{9'}$ are each independently selected from H and $C_{1-6}$ alkyl, or $R^9$ and $R^{9'}$ taken together are oxo; and
$R^{10}$ is —NH-L.

In certain embodiments, E of Formula (1) is selected from

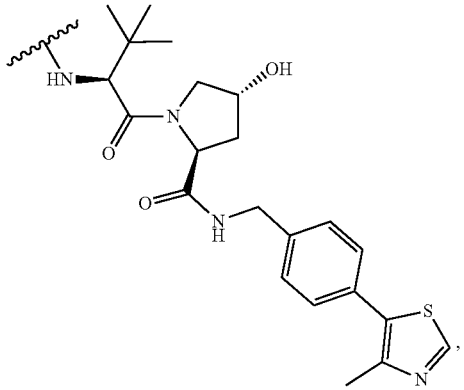

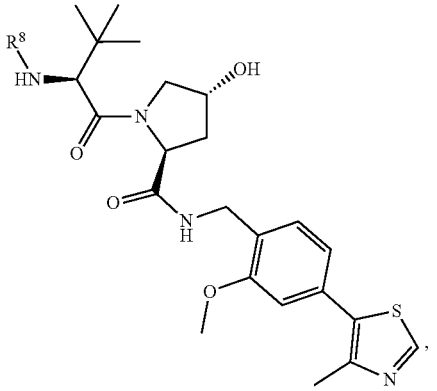

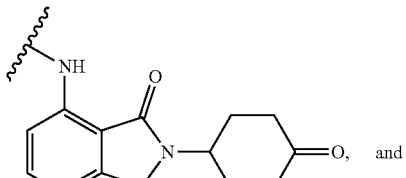, and

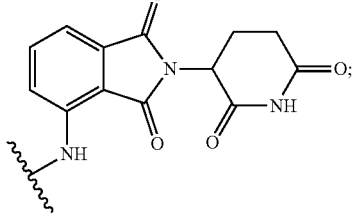;

wherein $R^8$ is selected from:

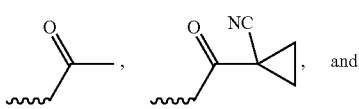, and

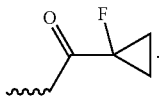.

In certain embodiments, the compound of Formula (1) is:
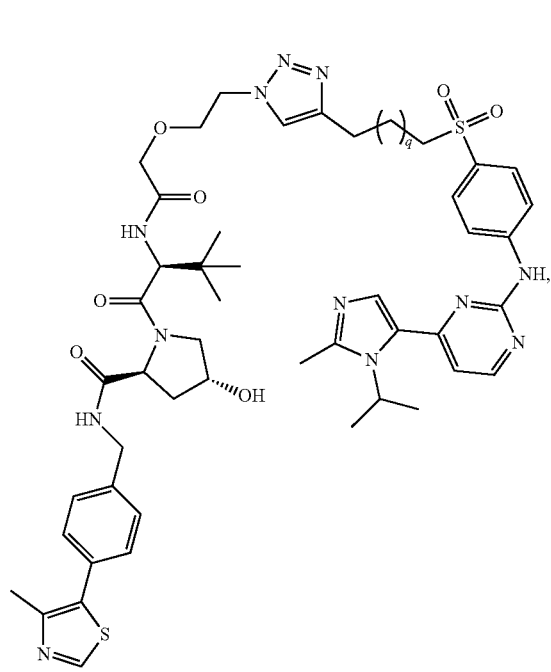
or a pharmaceutically acceptable salt thereof,
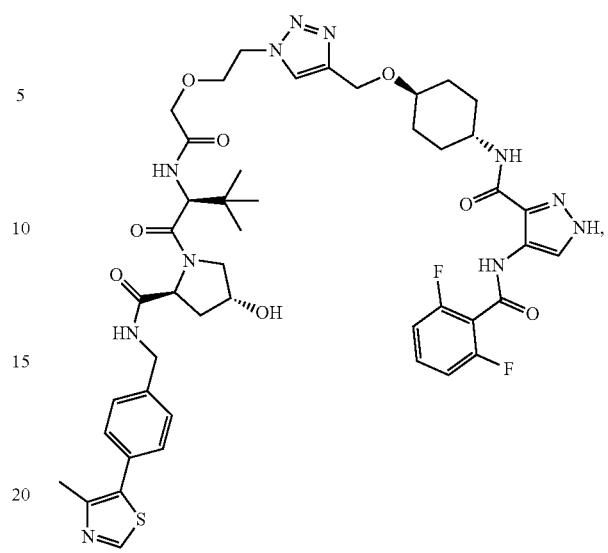
or a pharmaceutically acceptable salt thereof, or
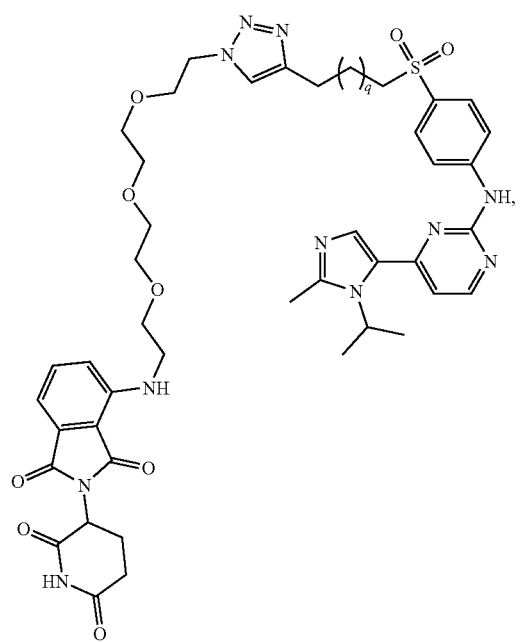
or a pharmaceutically acceptable salt thereof,
or a pharmaceutical salt thereof, wherein q is 0 or 1.

In certain embodiments, the compound of Formula (1) is:

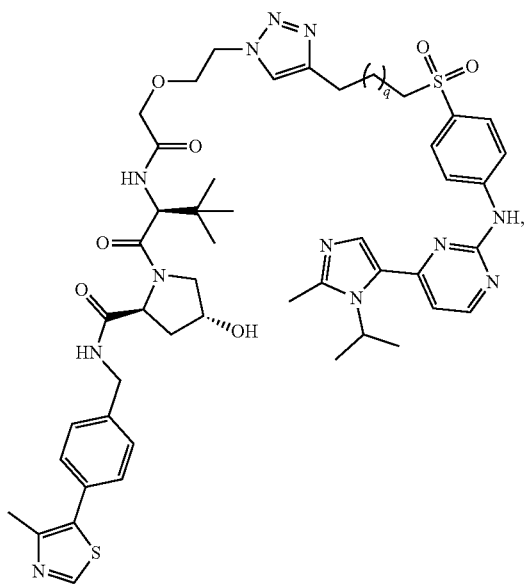

or a pharmaceutically acceptable salt thereof, wherein q is 1.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawings will be provided by the Office upon request and payment of the necessary fee.

FIG. 4A is a 1H NMR Spectrum of the compound of Example 1 (PROTAC-7); FIG. 4B is a 1H NMR Spectrum of the compound of Example 2 (PROTAC-8); FIG. 4C is a 1H NMR Spectrum of the compound of Example 3 (PROTAC-9); FIG. 4D is a 1H NMR Spectrum of the compound of Example 4 (PROTAC-10).

FIG. 6A) Representative immunoblots from HEI-OC1 cells treated with 0.1 nM to 1 μM of the compounds of Examples 1-4, AZD5438, or AT7519-7 for 24 hours. neg ctrl=Kidney lysate of CDK2 knock-out mice used as a negative control for CDK2 immunoblots only; FIG. 6B) HEI-OC1 cell lysates were immunoassayed for CDK1, CDK5, CDK7 and CDK9. β-actin was used as loading control; FIG. 6C) Quantification of the corresponding CDK2 bands from three independent experiments. Kruskal-Wallis followed by Dunn's post hoc test was used for comparison between the groups; *$P<0.05$; $P<0.01$; FIG. 6D**) Representative western blot of HEI-OC1 cell lysate after 24 hours of treatment with combinations of MG-132 and the compound of Example 2.

FIG. 8A) Ribbon representation of the energy-minimized structure of the pVHL-PROTAC-8-CDK2 ternary complex. pVHL (grey) connected through PROTAC-8 to CDK2 (orange); FIG. 8B) Definition of α1, α2, α3, and α4 dihedral angles used for determination of the relative movement of the two proteins in the ternary complex.

FIG. 9A) Distributions of α1 (black), α2 (red), and α3 (blue) dihedral angles for MD simulation 1; FIG. 9B) α4 dihedral angle in MD simulations 1 (black), 2 (red), 3 (blue), and 5 (green) is in gauche(−) conformations, whereas in MD simulation 5 (orange) α4 explored both gauche(+) and gauche(−) conformations. MD simulations 1 and 2 resulted in similar α4 dihedral angle distribution therefor the two curves are indistinguishable (black line is not visible because the red line is imposed over the black line).

FIG. 10A) In MD simulations 1-4 the two proteins move independently from each other and only intradomain movement can be observed; FIG. 10B) In MD simulation 5 both intradomain correlated and interprotein anti-corrleated movements are observed.

FIG. 11A: Five-day post-fertilization fish were pre-incubated for 1 hour with PROTAC-8 followed by a co-incubation for 6 hours with cisplatin 400 μM and PROTAC-8. Animals were processed for immunostaining and neuromast hair cell quantified. PROTAC alone did not show any toxic effect. FIG. 11B: Representative immunoblots of total zebrafish lysates treated as in A. Actin was used as a loading control. FIG. 11C: Quantification of zebrafish CDK2 abundance.

FIG. 12A) Representative immunoblots from the treatment of zebrafish with PROTAC-8 from 0.1 nM to 1 μM for 24 hours; FIG. 12B) Quantification of the corresponding CDK2 bands from three independent experiments. Kruskal-Wallis followed by Dunn's post hoc test was used for comparison between the groups where *P<0.05; P<0.01; FIG. 12C) The number of hair cells per neuromast was quantified after treatment with PROTAC-8 or AZD5438 in the presence or absence of 300 μM of Cisplatin. Results are expressed as mean±SEM. Statistical analysis: 1-way ANOVA with correction for Dunnett's multiple comparisons test. P<0.01; *P<0.001; P<0.0001 versus cisplatin treatment; Black bar: media-treated control; white bar: cisplatin-treated control; FIG. 12D) The number of hair cells per neuromast was quantified after pre-treatment with PROTAC-8 or AZD5438 followed by kainic acid (KA) 300 μM for 50 min. Results are expressed as mean±SEM. Statistical analysis: 1-way ANOVA with correction for Dunnett's multiple comparisons test. P<0.01; *P<0.001; P<0.0001 versus KA alone; FIG. 12E**) Representative images of 5 dpf zebrafish pretreated with PROTAC-8 (0.1 nM-1 μM) followed by incubation with KA.

DETAILED DESCRIPTION

Figure 1:
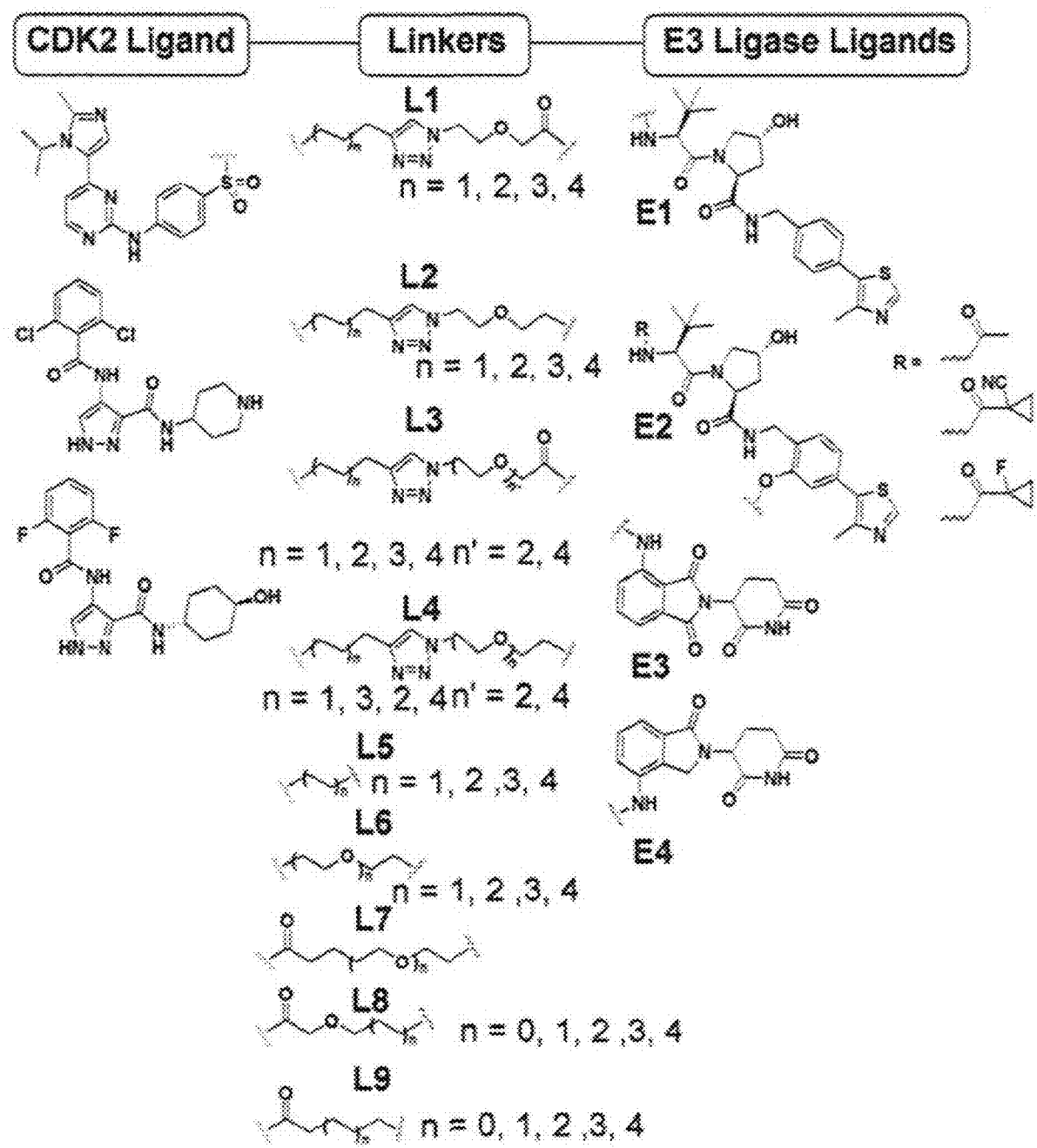
FIG. 1 shows exemplary embodiments of CDK2-PROTAC compounds disclosed herein for cancer therapy and hearing loss.
Figure 2:
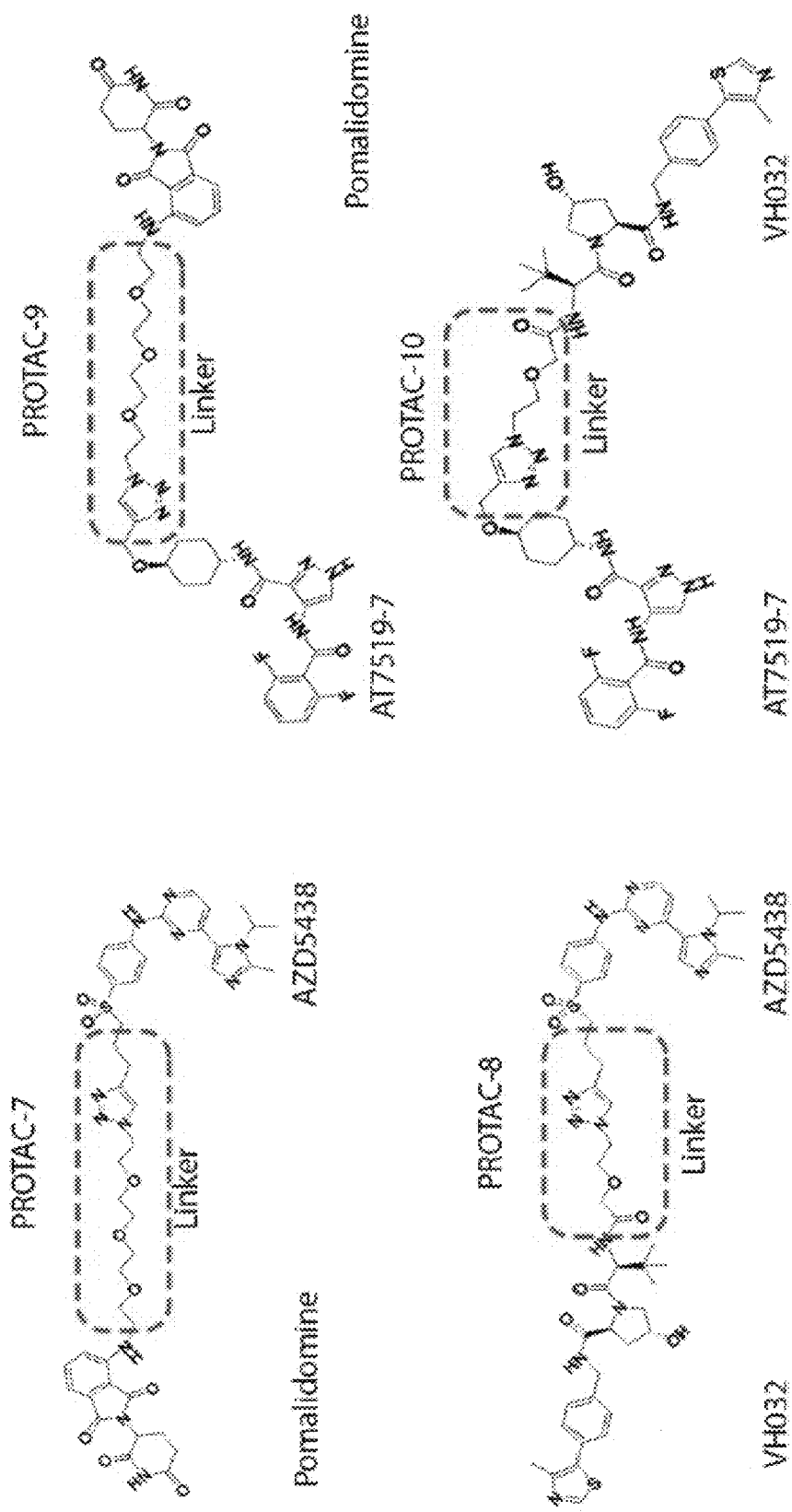
FIG. 2. PROTACs with CDK2 inhibitors (AZD5438 and AT7519-7), linkers and E3 ligase ligands (Pomalidomide and VH-032).

Disclosed herein are compounds, namely CDK2-PROTACs, that can be used for specific degradation of the cyclin-dependent kinase 2 (CDK2) protein, for treatment of cancers and other CDK2 related diseases as well as for prevention and treatment of hearing loss. Exemplary embodiments of the CDK2-PROTAC compounds are shown in FIG. 1. These compounds and their derivatives are derived small molecule CDK2 inhibitors (i.e., AZD5438, AT7519, and AT7519-7) and include linkers and E3 ligase recognition domains. PROTACs with CDK2 inhibitors (AZD5438 and AT7519-7), linkers and E3 ligase ligands (Pomalidomide and VH-032) are shown in FIG. 2. Pomalidomide and VH-032, have been well studied and by themselves did not show much toxic effects, while CRBN based degraders can recruit neo-substrate degradation (e.g., SALL4 for limb deformation) that can cause toxicity.

Figure 3:
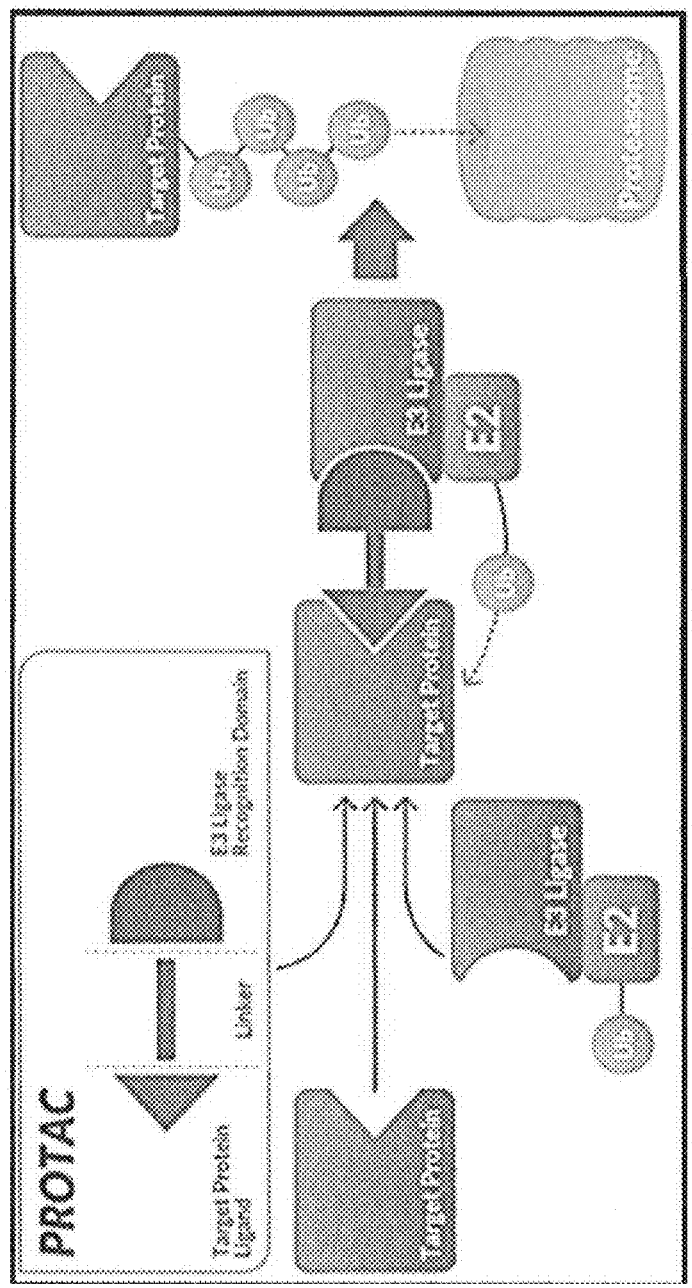
FIG. 3 shows an overview of the PROTACs system and mechanism of action.

FIG. 3 shows an overview of a PROTACs system and mechanism of action. A PROTAC molecule brings a target protein into contact with an E3 ubiquitin ligase, prompting transfer of ubiquitin (Ub) from an E2 ubiquitin conjugating enzyme, leading to polyubiquitination of the target protein and degradation by the proteasome.

In some embodiments, the compounds have been tested in cell lines and found to partially degrade CDK2 protein specifically but not CDK9 and CDK1, two closest relatives among CDKs. In an exemplary embodiment, the compounds were tested in zebrafish lateral line neuromasts in vivo and found that they protected against cisplatin induced hair cell loss in mouse chochlear explants and degrades CDK2 protein. Also disclosed herein is a method of treating cancer or any CDK2 protein related disease and for prevention and treatment of hearing loss caused by various acoustic insults (i.e., antibiotics, cisplatin, noise, and aging), including administering a therapeutically effective amount of the disclosed compounds.

In certain embodiments, the cancer is prostate cancer, colon cancer, breast cancer, ovarian cancer, lung cancer, melanoma, myeloma, glioblastoma, lymphoma, or hepatocellular carcinoma.

Also provided herein is a method of synthesizing the CDK2-PROTAC compounds. In some embodiments, the method includes a click chemistry reaction.

In some embodiments, the CDK2-PROTAC compound is a compound having the structure of Formula (1):

X-L-E (1)

wherein X is a cyclin-dependent kinase 2 binding moiety;
L is a linking group selected from alkylene, (alkylene oxide)$_n$-alkylene, —C(=O)-alkylene, —C(=O)-alkylene-(alkylene oxide)$_n$-alkylene, —(C=O)-alkylene-O-alkylene, alkylene-(heteroaryl)-(alkylene oxide)$_m$-alkylene-C(=O)—, and alkylene-(heteroaryl)-(alkylene oxide)$_m$-alkylene;
wherein n and m are each independently an integer between 1 and 10; and
E is a ubiquitin ligase binding moiety.

CDK2 Binding Moiety

A "cyclin-dependent kinase 2 binding moiety" (CDK2 binding moiety) as used herein, refers to a ligand that can bind to the CDK2 protein. In some embodiments, the cyclin-dependent kinase 2 binding moiety X is selected from:

a compound having a structure of Formula (2):

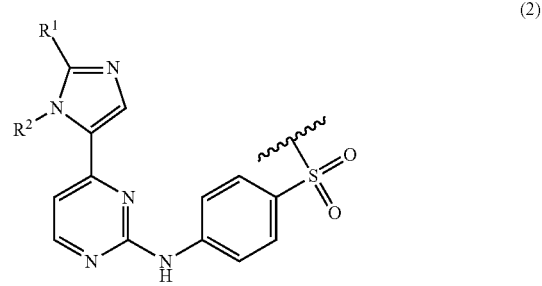

wherein $R^1$ and $R^2$ are each independently H, halo, or $C_{1-6}$ alkyl; and a compound having a structure of Formula (3):

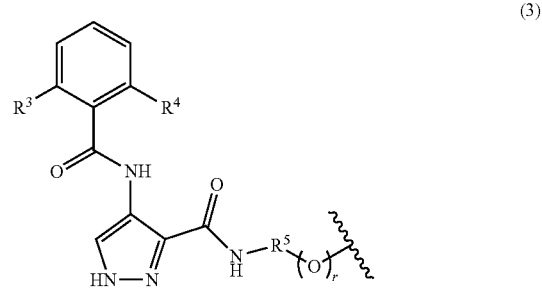

wherein $R^3$ and $R^4$ are each independently H, halo, or $C_{1-6}$ alkyl,
$R^5$ is selected from a 5-10 membered cycloalkyl or a 5-10 membered heterocycloalkyl,
and r is 0 or 1.

In some embodiments, X is a compound having the structure of Formula (2). In some embodiments, $R^1$ is $C_{1-6}$ alkyl. In some embodiments, $R^1$ is $C_{1-3}$ alkyl. In some embodiments, $R^2$ is $C_{1-6}$ alkyl. In some embodiments, $R^2$ is $C_{1-3}$ alkyl. In some embodiments, $R^1$ and $R^2$ are each independently $C_{1-6}$ alkyl. In some embodiments, $R^1$ and $R^2$ are each independently $C_{1-3}$ alkyl. In some embodiments, $R^1$ is methyl. In some embodiments, $R^2$ is isopropyl. In some embodiments, $R^1$ is methyl and $R^2$ is isopropyl.

In some embodiments, X is a compound having the structure of Formula (3). In some embodiments, $R^3$ is halo. In some embodiments, $R^3$ is Cl or F. In some embodiments, $R^3$ is Cl. In some embodiments, $R^3$ is F. In some embodiments, $R^4$ is halo. In some embodiments, $R^4$ is Cl or F. In some embodiments, $R^4$ is Cl. In some embodiments, $R^4$ is F. In some embodiments, $R^3$ and $R^4$ are each halo. In some embodiments, $R^3$ and $R^4$ are each independently Cl or F. In some embodiments, $R^3$ and $R^4$ are each Cl. In some embodiments, $R^3$ and $R^4$ are each F.

In some embodiments, $R^5$ selected from a 5-7 membered cycloalkyl or a 5-7 membered heterocycloalkyl. In some embodiments, $R^5$ selected from a 5-6 membered cycloalkyl or a 5-6 membered heterocycloalkyl. In some embodiments, $R^5$ is a 5-6 membered cycloalkyl. In some embodiments, $R^5$ is cyclohexyl. In some embodiments, $R^5$ is a 5-6 membered cycloalkyl and r is 1. In some embodiments, $R^6$ is a 5-6-membered heterocycloalkyl. In some embodiments, $R^6$ is piperidinyl. In some embodiments, $R^6$ is piperidinyl and r is 0.

In some embodiments, X is selected from:

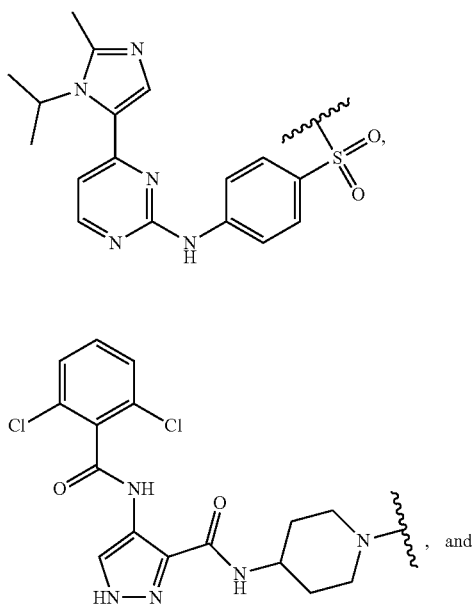

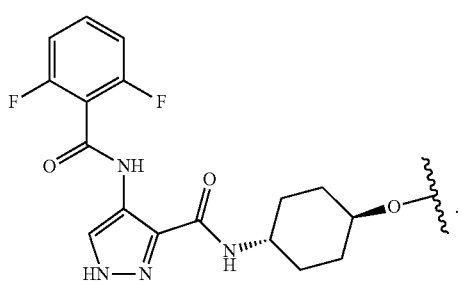

In some embodiments, X is AZD5438, having the structure

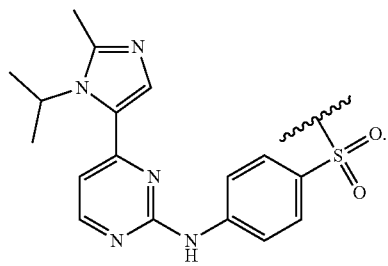 [SMILES: *S(=O)(=O)c1ccc(Nc2nccc(-c3cnc(C)n3C(C)C)n2)cc1]

In some embodiments, X is AT7519, having the structure

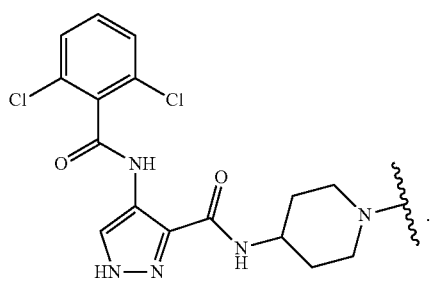 [SMILES: *N1CCC(NC(=O)c2n[nH]cc2NC(=O)c2c(Cl)cccc2Cl)CC1]

In some embodiments, X is AT7519-7, having the structure

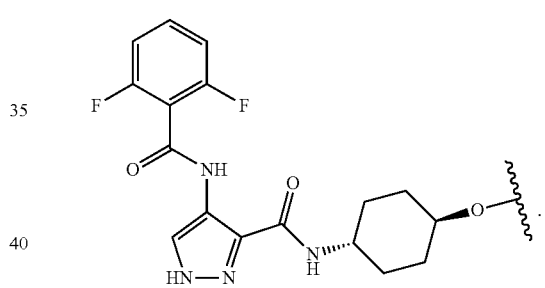

Linking Group

In some embodiments, the linking group L is selected from $C_{1-20}$ alkylene, $(C_{2-3}$ alkylene oxide$)_n$-$C_{2-3}$ alkylene, —C(=O)—$C_{1-20}$ alkylene, —C(=O)—$C_{2-3}$ alkylene-$(C_{2-3}$ alkylene oxide$)_n$-$C_{2-3}$ alkylene, —C(=O)—$C_{1-3}$ alkylene-O—$C_{2-20}$ alkylene, $C_{1-20}$ alkylene-(3-10 membered heteroaryl)-$(C_{2-3}$ alkylene oxide$)_m$-$C_{1-3}$ alkylene-C(=O)—, and $C_{1-20}$ alkylene-(3-10 membered heteroaryl)-$(C_{2-3}$ alkylene oxide$)_m$-$C_{2-3}$ alkylene.

In some embodiments, L is selected from $C_{1-8}$ alkylene, (ethylene oxide$)_n$-$C_{2-3}$ alkylene, —C(=O)—$C_{1-10}$ alkylene, —C(=O)—$C_{2-3}$ alkylene-(ethylene oxide$)_n$-$C_{2-3}$ alkylene, —(C=O)—$CH_2$—O—$C_{1-10}$ alkylene, $C_{1-10}$ alkylene-(3-7 membered heteroaryl)-(ethylene oxide$)_m$-$CH_2$—C(=O)—, and $C_{1-10}$ alkylene-(3-7 membered heteroaryl)-(ethylene oxide$)_m$-$C_{2-3}$ alkylene.

In some embodiments, L is $C_{1-10}$ alkylene-(3-7 membered heteroaryl)-(ethylene oxide$)_m$-$CH_2$—C(=O)—. In some embodiments, L is $C_{1-9}$ alkylene-(5-6 membered heteroaryl)-(ethylene oxide$)_m$-$CH_2$—C(=O)—. In some embodiments, L is $C_{1-9}$ alkylene-(triazolyl)-(ethylene oxide$)_m$-$CH_2$—C(=O)—.

In some embodiments, L is $C_{1-10}$ alkylene-(3-7 membered heteroaryl)-(ethylene oxide$)_m$-$C_{2-3}$ alkylene. In some embodiments, L is C$_{1-9}$ alkylene-(5-6 membered heteroaryl)-(ethylene oxide)$_m$-C$_{2-3}$ alkylene. In some embodiments, L is C$_{1-9}$ alkylene-(triazolyl)-(ethylene oxide)$_m$-C$_{2-3}$ alkylene.

In some embodiments, n and m are each independently an integer between 1 and 8. In some embodiments, n and m are each independently an integer between 1 and 6. In some embodiments, n and m are each independently an integer between 1 and 4.

In some embodiments, L is selected from:

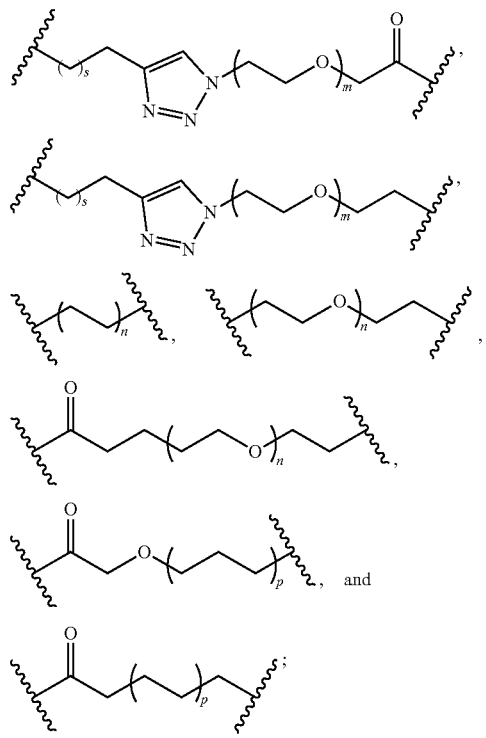

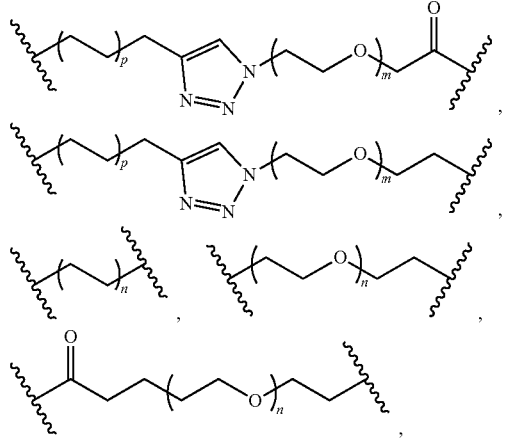

wherein n is an integer between 1 and 4, m is an integer between 1 and 4, and p is an integer between 0 and 4, and s is an integer between 0 and 8.

In some embodiments, L is selected from:

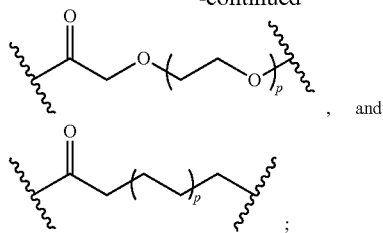

wherein n is an integer between 1 and 4, m is an integer between 1 and 4, and p is an integer between 0 and 4. In some embodiments, p is 1, 2, 3, or 4. In some embodiments, m is 1, 2 or 4. In some embodiments, m is 2 or 4. In some embodiments, p is 1, 2, 3, or 4 and m is 1, 2, or 4. In some embodiments, p is 1, 2, 3, or 4 and m is 2 or 4. In some embodiments, p is 1, 2, or 4. In some embodiments, p is 1, 2 or 4 and m is 1, 2, or 4. In some embodiments, p is 1, 2, or 4 and m is 2 or 4.

In some embodiments, L is selected from:

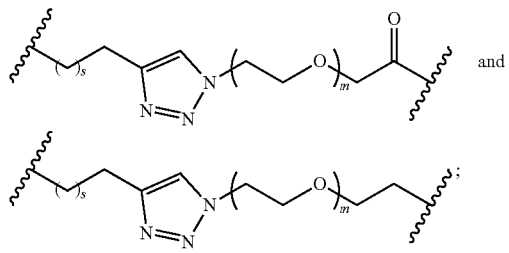

wherein m is an integer between 1 and 4, and s is an integer between 0 and 8. In some embodiments, m is an integer between 1 and 3, and s is an integer between 0 and 4. In some embodiments, m is an integer between 1 and 3, and s is an integer between 0 and 2. In some embodiments, m is 1 or 3, and s is 0, 1, or 2.

In some embodiments, L is selected from:

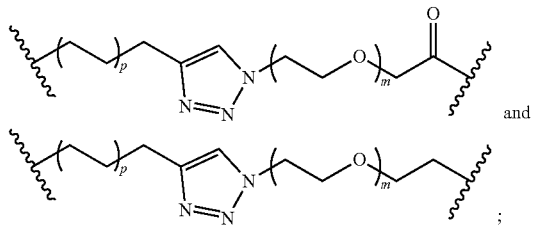

wherein p is 0, 1, 2, or 4, and m is an integer between 2 and 4.

In some embodiments, L is

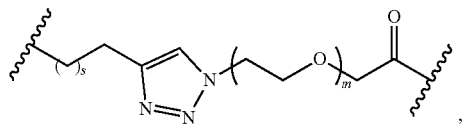

wherein m is an integer between 1 and 4, and s is an integer between 0 and 8. In some embodiments, m is an integer between 1 and 3, and s is an integer between 0 and 4. In some embodiments, m is an integer between 1 and 3, and s is an integer between 0 and 2. In some embodiments, m is 1 or 3, and s is 0, 1, or 2. In some embodiments, m is 1 and s is 0, 1, or 2. In one embodiment, m is 1 and s is 0.

In one embodiment, m is 1 and s is 1. In one embodiment, m is 1 and s is 2.

In some embodiments, L is

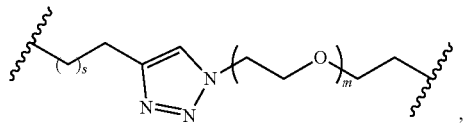

wherein m is an integer between 1 and 4, and s is an integer between 0 and 8. In some embodiments, m is an integer between 1 and 3, and s is an integer between 0 and 4. In some embodiments, m is an integer between 1 and 3, and s is an integer between 0 and 2. In some embodiments, m is 1 or 3, and s is 0, 1, or 2. In some embodiments, m is 3 and s is 0, 1, or 2. In one embodiment, m is 3 and s is 0. In one embodiment, m is 3 and s is 1. In one embodiment, m is 3 and s is 2.

In another embodiment, the linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by a group independently selected from (—O—) and heteroaryl (e.g. a divalent triazole), and wherein the chain is optionally substituted on carbon with one or more (e.g. 1, 2, 3, or 4) substituents selected from halo, hydroxy, and oxo (=O).

Ubiquitin Ligase Binding Moiety

A "ubiquitin ligase binding moiety," as used herein, refers to a ligand that can bind to the E3 ubiquitin ligase protein. In some embodiments, the ubiquitin ligase binding moiety E is selected from:

a compound having a structure of Formula (4):

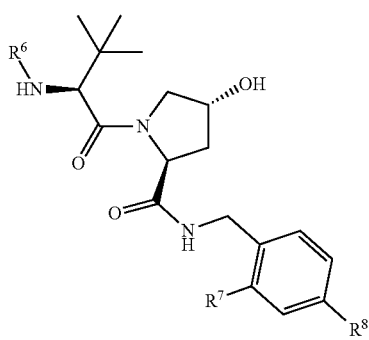

(4)

wherein $R^6$ is selected from a bond linking to L and —C(=O)$R^{6a}$, wherein $R^{6a}$ is selected from H, $C_{1-6}$ alkyl, and $C_{3-6}$ cycloalkyl optionally substituted with 1-3 $R^{6b}$ groups, wherein $R^{6b}$ is selected from $C_{1-6}$ alkyl, halo, and CN;

$R^7$ is selected from H, $C_{1-6}$ alkyl, and —O— linked to L; and $R^8$ is a 3-7 membered heteroaryl optionally substituted with 1-5 $R^{8A}$ substituents, wherein each $R^{8A}$ is independently $C_{1-6}$ alkyl; and a compound having a structure of Formula (5):

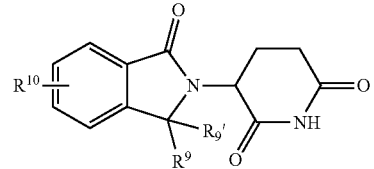

(5)

wherein $R^9$ and $R^{9'}$ are each independently selected from H and $C_{1-6}$ alkyl, or $R^9$ and $R^{9'}$ taken together are oxo; and $R^{10}$ is —NH— linked to L.

In some embodiments, E is a compound of Formula (4). In some embodiments, $R^6$ is L. In some embodiments, $R^6$ is —(C=O)$R^{6a}$. In some embodiments, $R^{6a}$ is $C_{1-6}$ alkyl. In some embodiments, $R^{6a}$ is $C_{1-3}$ alkyl. In some embodiments, $R^{6a}$ is methyl. In some embodiments, $R^{6a}$ is $C_{3-6}$ alkyl. In some embodiments, $R^{6a}$ is cyclopropyl. In some embodiments, $R^{6a}$ is cyclopropyl substituted with 1 $R^{6b}$ group. In some embodiments, $R^{6b}$ is $C_{1-6}$ alkyl. In some embodiments, $R^{6b}$ is $C_{1-3}$ alkyl. In some embodiments, $R^{6b}$ is methyl. In some embodiments, $R^{6b}$ is halo. In some embodiments, $R^{6b}$ is F.

In one embodiment, the compound of Formula (1) is a compound of the following Formula (1a):

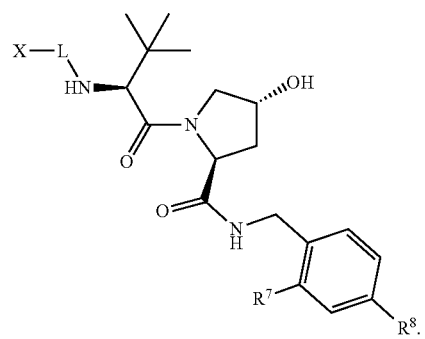

(1a)

In one embodiment, the compound of Formula (1) is a compound of the following Formula (1b):

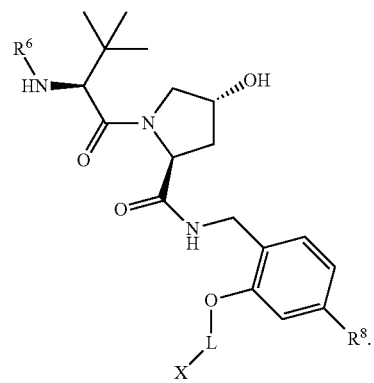

(1b)

In one embodiment, the compound of Formula (1) is a compound of the following Formula (1c):

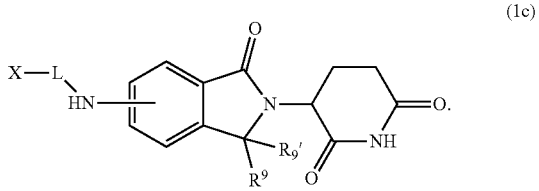

(1c)

It is appreciated that certain features of the invention, which are, for clarity, described in the context of separate embodiments, can also be provided in combination in a single embodiment as if the embodiments were claims written in multiple dependent form. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

In one embodiment, heteroaryl is a 5-membered or 6-membered aromatic ring comprising one or more (e.g., 1, 2, or 3) heteroatoms. In one embodiment, heteroaryl is a 5-membered or 6-membered aromatic ring comprising one or more (e.g., 1, 2, or 3) nitrogen atoms. In one embodiment, heteroaryl is a 5-membered or 6-membered aromatic ring comprising two or three nitrogen atoms. In one embodiment, heteroaryl is a triazole ring.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the term "independently selected from" means that each occurrence of a variable or substituent are independently selected at each occurrence from the applicable list.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl," employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (i-Pr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "halo" refers to F, Cl, Br, or I. In some embodiments, halo is F, Cl, or Br. In some embodiments, halo is F. In some embodiments, halo is Cl. In some embodiments, halo is Br.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heterocycloalkyl" refers to a monocyclic or polycyclic ring (e.g., having 2, 3, or 4 fused rings) having at least one non-aromatic ring (saturated or partially unsaturated ring), wherein one or more of the ring-forming carbon atoms of the heterocycloalkyl is replaced by a heteroatom selected from N, O, or S, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 4-10-, 5-10, 4-7-, and 5-6-membered heterocycloalkyl groups. Heterocycloalkyl groups can also include spirocycles and bridged rings. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 4 to 10 ring-forming atoms, 4 to 7 ring-forming atoms, 4 to 6 ring-forming atoms or 5 to 6 ring-forming atoms. In some embodiments, the heterocycloalkyl group has 1 to 4 heteroatoms, 1 to 3 heteroatoms, 1 to 2 heteroatoms or 1 heteroatom.

In some embodiments, the heterocycloalkyl is a 4-10 membered monocyclic, bicyclic, or tricyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-10 membered bicyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-7 membered monocyclic heterocycloalkyl having 1 or 2 ring-forming heteroatoms independently selected from N, O, and S, and wherein 1, 2 or 3 ring-forming carbon or heteroatoms can be optionally substituted by one or more oxo or sulfido. In some embodiments, the heterocycloalkyl is a monocyclic 4-6 membered heterocycloalkyl having 1 or 2 heteroatoms independently selected from N, O, S, and B and having one or more oxidized ring members.

Examples of heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, dihydrothiophenyl, piperidinyl, pyrrolidinyl, morpholinyl, thiomorpholinyl, isoxazolidinyl, isothiazolidinyl, pyrazolidinyl, oxazolidinyl, thiazolidinyl, imidazolidinyl, caprolactamyl, azepanyl, diazepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, azabicyclo[2.2.1]heptan-7-yl, azabicyclo[2.2.1]heptan-2-yl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, oxa-azaspiro[3.4]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, dihydrobenzo[1,4]oxazepinyl, and the like.

As used herein, the term "alkylene" refers a divalent straight chain or branched alkyl linking group. Examples of "alkylene groups" include methylene, ethan-1,1-diyl, ethan-1,2-diyl, propan-1,3-diyl, propan-1,2-diyl, propan-1,1-diyl and the like.

As used herein, the term "(alkylene oxide)$_m$" refers to a group of the following general structure: (-alkylene-O—)$_m$. Examples of "(alkylene oxide)$_m$" groups include (ethylene oxide)$_m$, which has the formula

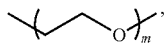

and (propylene oxide)$_m$, which has the formula

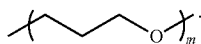

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

EXAMPLES

The compounds and methods of the present disclosure are further described in the following examples, which do not limit the scope of the claims.

Experimental Methods

Chemistry

All reactions were carried out in flame-dried flasks with magnetic stirring. Unless otherwise noted, all experiments were performed under a nitrogen atmosphere. All reagents were purchased from Sigma Aldrich, Acros Organics, Fisher Scientific, or Alfa Aesar. Solvents were treated with 4 Å molecular sieves and distilled before use. Purifications of reaction products were carried out by column chromatography using Chem Lab silica gel (230-400 mesh). $^1$H NMR spectra were recorded with tetramethylsilane (TMS) as internal standard at ambient temperature unless otherwise indicated Bruker 500 MHz for $^1$H NMR (FIGS. 4A-4D). Chemical shifts are reported in parts per million (ppm) and coupling constants are reported as Hertz (Hz). Splitting patterns are designated as singlet (s), broad singlet (bs), doublet (d), triplet (t). Splitting patterns that could not be interpreted or easily visualized are designated as multiple (m). Final compounds used in the study were more than 95% pure.

HEI-OC1 Experiments

HEI-OC1 cells were maintained in DMEM with 10% of Fetal bovine serum at 33° C. in a 10% $CO_2$ atmosphere. Cells were plated in 6-well plates (60,000 cells per well) 24 hours before the initiation of the experiment and then incubated for an additional 24 hours with 0.1 nM to 1 µM of PROTACS 7-10, AZD5438 or AT519-7. Cells were harvested in RIPA buffer (NaCl 150 mM, Tris-HCl 50 mM, Nonidet-40 1%, Sodium deoxycholate 0.5%, SDS 0.1%, pH 7.4) containing protease (Sigma-Aldrich, MO P8340) and phosphatase inhibitors (ThermoFisher, CA, A32957) for immunoblot analysis.

In the case of the proteasome inhibitory studies, HEI-OC1 cells were incubated with PROTAC-8 100 nM with or without MG-132 (300 nM, Calbiochem, MO, 474790), for 24 hours. Lysates were prepared after a 24 hours incubation and processed for Western blot analysis.

Animals

Four days post-fertilization (dpf) zebrafish (*Danio rerio*) larvae were obtained by pair mating of adult TuAB fish maintained at Creighton University by standard methods approved by the Institutional Animal Care and Use Committee. Experimental fish were maintained at 28.5° C. in E3 media (5 mM NaCl, 0.17 mM KCl, 0.33 mM $CaCl_2$ and 0.33 nM $MgSO_4$, pH 7.2) until the day of the experiment.

In Vivo Experiments

Cisplatin studies: Four days post-fertilization (dpf) fish were pre-incubated with different concentrations of PROTAC-8 or AZD5438 (0.1 nM to 10 µM) for 24 hrs in E3 media. The next day animals were co-incubated with PROTAC-8 or AZD5438 and cisplatin (Millipore Sigma, 479306) 300 µM for 6 hours.[57] At the end of the incubation, fish were transferred to fresh E3 media, led to recover for 1 hour, and fixed overnight with 4% paraformaldehyde. Animals were immunostained for the hair cell marker, otoferlin (HCS-1, DSHB), and process for fluorescence microscopy. Otic, middle, and opercular neuromasts were identified, and hair cells were manually counted using a Zeiss AxioSkop 2 fluorescence microscope with a 40× oil objective.

Kainic acid studies: Fish was pre-incubated with PROTAC-8 or AZD5438 as described above. The next day fish were transferred to a fresh solution of kainic acid 300 μM for 50 min, led recover in fresh E3 media for 2 hours, and fixed with 4% paraformaldehyde. Animals were processed for immunofluorescence analysis as described for the cisplatin treatments. After the 24 hours incubation with PROTAC-8 and before the incubation with the ototoxin, some fish were collected for immunoblot analysis of CDK2 abundance.

Stock solutions for PROTAC-8, AZD5438, and cisplatin were prepared in DMSO. Control animals were exposed to 0.1% DMSO in E3 media. Images were taken employing a Zeiss LSM 710 confocal microscope with a 63× oil objective.

CDKs Immunoblot Assays

For the calculation of CDKs abundance, immunoblots were performed in HEI-OC1 cells and zebrafish treated with PROTACS as described before.[57] Briefly, 20-30 μg of protein were used per lane. Membranes were blocked for 1 hour at room temperature with 3% milk followed by overnight incubation with the primary antibody in 3% milk. After several washes and the secondary incubation for 1 hour, membranes were developed employing an iBright FL1000 (ThermoFisher, CA). Immunoblots were stripped and probed for β-actin as the loading control. Specific bands were quantified using ImageJ (NIH).

Primary antibodies: rabbit anti-CDK2 dilution 1:500 (CST, MA, #2546), rabbit anti-CDK5 dilution 1:1,000 (CST, MA, #2506), rabbit anti-CDK9 dilution 1:1,000 (CST, MA, #2316), rabbit anti-CDK1 dilution 1:1,000 (ABclonal, MA, #A11420), mouse anti-β-actin dilution 1:2,000 (Sigma-Aldrich, MO, A5441).

Confocal Imaging

For the screening of the effect of PROTAC-8, neuromast hair cell counts were performed manually, employing a Zeiss AxioSkop 2 fluorescence microscope with a 40× oil objective. Confocal imaging was performed using a Zeiss LSM 710 confocal laser scanning image system with a 63× oil objective. Images were captured at room temperature with automatically set sectioning. The acquired images were processed with ZEN black edition software. Z-stack images are presented as flat Z-projections.

Molecular Dynamics (MD) Simulations

Using the X-ray structures of the CDK2-AZD5438 complex (PDB i.d. 6GUE) and the pVHL-VH-032 complex (PDB i.d. 5NW0) PROTAC-8 was built on the 6GUE structure in YASARA (Krieger, E.; Vriend, G., New ways to boost molecular dynamics simulations. *J. Comput. Chem.* 2015, 36, 996-1007) and the apo-pVHL was docked on the complex. The structure of the pVHL-PROTAC-8-CDK2 ternary complex was then energy-minimized using the AMBERff14SB (Maier, J. A.; Martinez, C.; Kasavajhala, K.; Wickstrom, L.; Hauser, K. E.; Simmerling, C., ff14SB: Improving the Accuracy of Protein Side Chain and Backbone Parameters from ff99SB. *J. Chem. Theory. Comput.* 2015, 11, 3696-3713) and the GAFF[59] (Wang, J.; Wolf, R. M.; Caldwell, J. W.; Kollman, P. A.; Case, D. A., Development and testing of a general amber force field. *J. Comput. Chem.* 2004, 25, 1157-1174) parameter sets. After energy minimization, the pVHL-PROTAC-8-CDK2 ternary complex was solvated with 154 mM aqueous NaCl solution in an 11.3 nm×11.3 nm×11.3 nm cubic box and the energy of the system was minimized again. MD simulations (100 ns) were performed in an NPT ensemble at 1 atm pressure and 310 K. Integration time was 2 fs, bonds for pVHL-PROTAC-8-CDK2 ternary complex and water were constrained with the LINCS[60] (Hess, B.; Bekker, H.; Berendsen, H. J. C.; Fraaije, J. G. E. M., LINCS: A linear constraint solver for molecular simulations. *J. Comput. Chem.* 1997, 18, 1463-1472) and SETTLE[61] (Miyamoto, S.; Kollman, P. A., Settle: An analytical version of the SHAKE and RATTLE algorithm for rigid water models. *J. Comput. Chem.* 1992, 13, 952-962) algorithm, respectively. The non-bonded cut-off was 0.8 nm and the long-range electrostatic was treated with the PME method. Essman, U.; Perera L.; Berkowitz, M. L., A smooth particle mesh Ewald method. *J. Chem. Phys.* 1995, 103, 8577-8593.

Statistics

For HEI-OC1 cells and fish experiments, one-way ANOVA followed by Dunnett's multiple comparisons test was performed using GraphPad Prism version 8.2.0 software. P values less than 0.05 were considered significant. Results are expressed as mean±SEM. For the experiments performed with fish, 6-8 fish were used per experiment. Western blots were performed 2 to 3 times employing 3 different biological replicates. Zebrafish experiments were performed 3 times.

Examples 1-4

From our previous study (Hazlitt, R. A.; Teitz, T.; Bonga, J. D.; Fang, J.; Diao, S.; Iconaru, L.; Yang, L.; Goktug, A. N.; Currier, D. G.; Chen, T.; Rankovic, Z.; Min J.; Zuo, J., Development of Second-Generation CDK2 Inhibitors for the Prevention of Cisplatin-Induced Hearing Loss. *J. Med. Chem.* 2018, 61, 7700-7709), we selected the two best CDK2 inhibitors, AZD5438 and AT7519-7 as our CDK2-targeting ligands for PROTAC design since they exhibit the best protection against cisplatin-induced ototoxicity in mouse cochlear explants and in vivo mouse models (Table 1).

TABLE 1

PROTACs with CDK2 inhibitors (AZD5438 and AT7519-7), linkers and E3 ligase ligands (Pomalidomide and VH-032)

| Ex. | Compound | CDK2 Ligand | Linker | E3 Ligand |
|---|---|---|---|---|
| 1 | PROTAC-7 | AZD5438 | 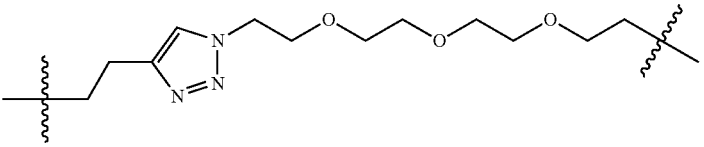 [SMILES: *CCOCCOCCOCCn1cc(CC*)nn1] | Pomalidomide |

TABLE 1-continued

PROTACs with CDK2 inhibitors (AZD5438 and AT7519-7), linkers and E3 ligase ligands (Pomalidomide and VH-032)

| Ex. | Compound | CDK2 Ligand | Linker | E3 Ligand |
|---|---|---|---|---|
| 2 | PROTAC-8 | AZD5438 | | VH032 |
| 3 | PROTAC-9 | AT7519-7 | | Pomalidomide |
| 4 | PROTAC-10 | AT7519-7 | | VH032 |

In the design of PROTAC, the choice of E3 ligase and the selection of target ligands and their conjugation are critical optimization variables. The most common ligases successfully used in the design of PROTAC molecules are the von Hippel-Lindau (VHL) protein complex $CRL2^{VHL}$ and the Cereblon (CRBN) complex $CRL4^{CRBN}$. Studies have shown that PROTACs made of the same target ligand but either VHL or CRBN ligands can exhibit different degradation selectivity and efficacy. In some systems, CRBN-based degraders showed higher degradation efficiency or selectivity than VHL-based analogs. These observations influenced us to develop VHL- and CRBN-based degraders in parallel.

Accordingly, a focused library of four PROTAC degraders was synthesized by combining the CDK2 ligands with variable linkers (See Schemes 1 and 2). The use of two proven E3 ligase recognition ligands, pomalidomide and VH-032, for CRBN and VHL, respectively, also ensures non-toxicity and high effectiveness of our strategy (Table 1).

Scheme 1 shows the synthesis of Examples 1 and 2. Reagents and conditions are as follows: (a) DMF, rt, 36 h; (b) NAOtBu (3.0 equiv.), BINAP (0.1 equiv.), $Pd_2(dba)_3$ (0.05 equiv.), 1,4-Dioxane, 80° C., 2 h; (c) $CuSO_4$ (1.1 equiv.), Sodium ascorbate (2.2 equiv.), DMSO:$H_2O$ (1:1), rt, 20 h.

Scheme 1. Synthesis of Examples 1 and 2.

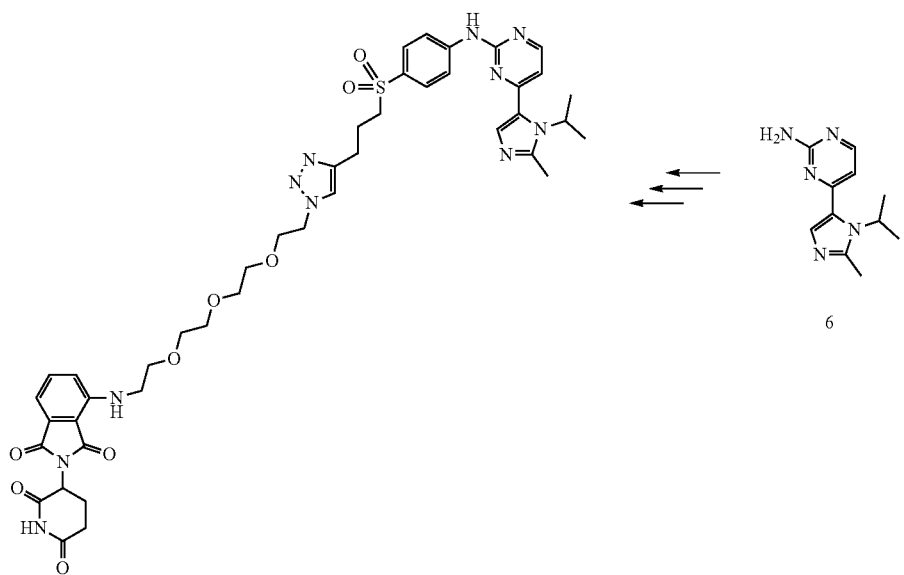

PROTAC-7

-continued

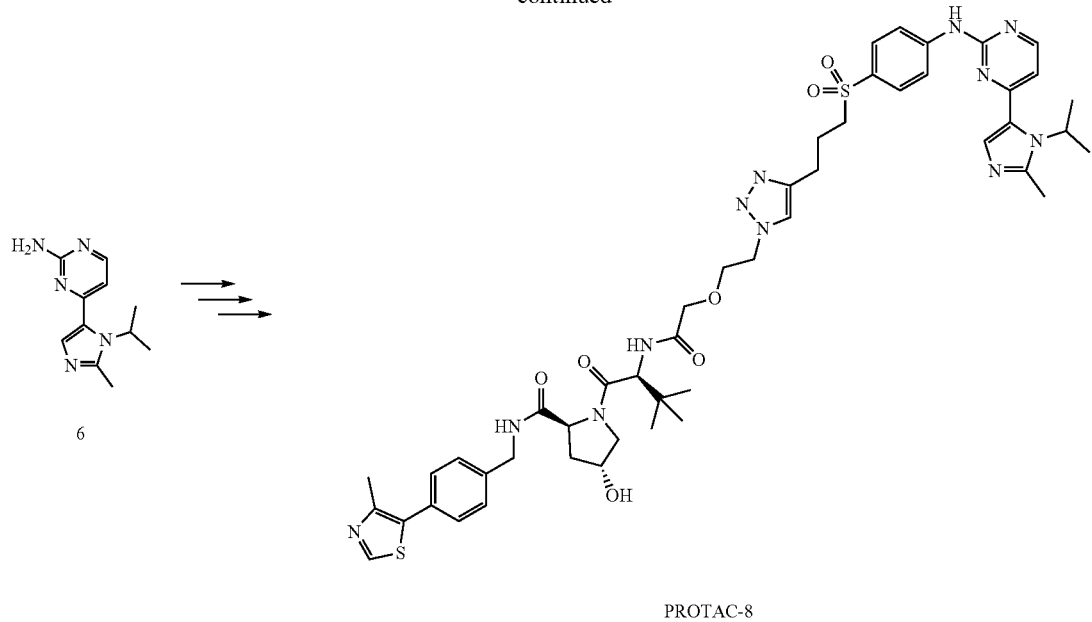

PROTAC-8

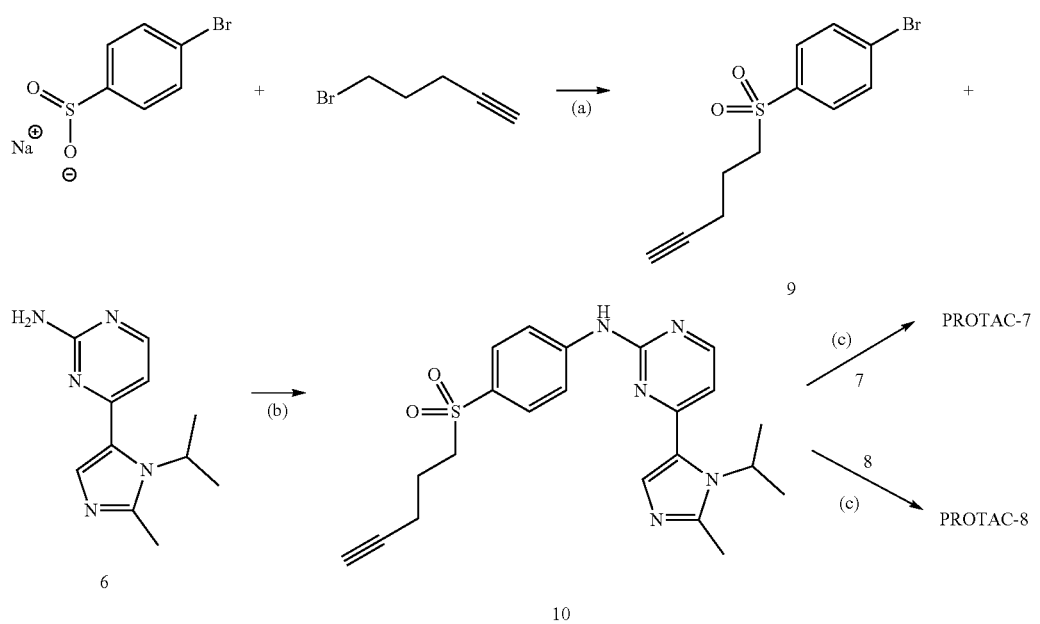

Scheme 2 shows the synthesis of Examples 3 and 4. Reagents and conditions are as follows: (a) EDC (1.2 equiv.), HOBt (1.2 equiv.), DMF, rt, 20 h; (b) NaOH/EtOH (2M), rt, 20 h; (c) (1r,4r)-4-(prop-2-yn-1-yloxy)cyclohexan-1-amine (1.0 equiv.), EDC (1.2 equiv.), HOBt (1.2 equiv.), DMF, rt, 18 h; (d) 2-(2-(2-(2-azidoethoxy)ethoxy)ethoxy)ethan-1-amine (1.0 equiv.), DIPEA (2.0 equiv.), DMF, 90° C., 18 h; (e) 2-(2-azidoethoxy)acetic acid (1.0 equiv.), DIPEA (6.0 equiv.), HATU (4.0 equiv.), DMF, 0° C.-rt, 20 min; (f) $CuSO_4$ (1.1 equiv), Sodium ascorbate (2.2 equiv.), DMSO:$H_2O$ (1:1), rt, 20 h.

Scheme 2. Synthesis of Examples 3 and 4.
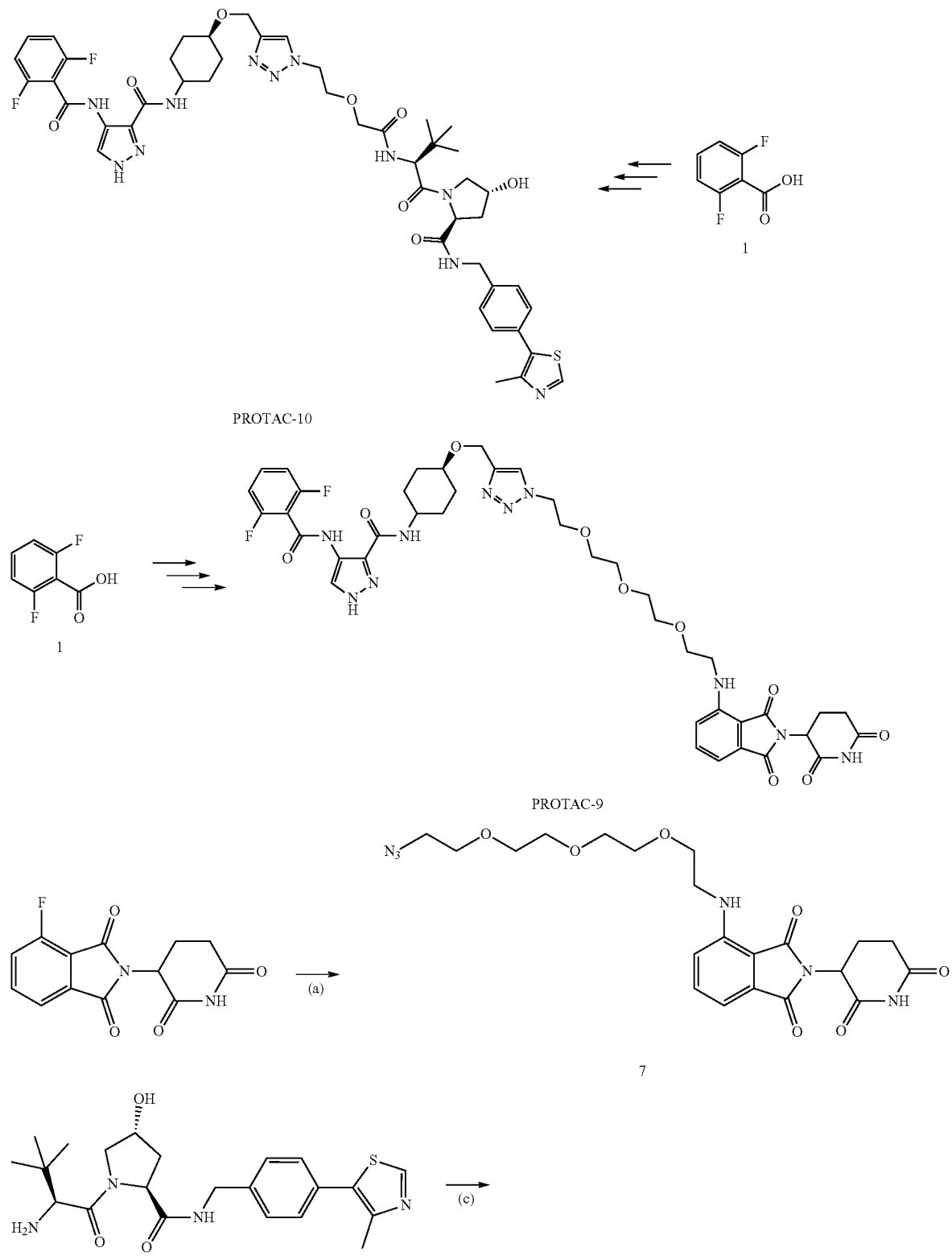

-continued

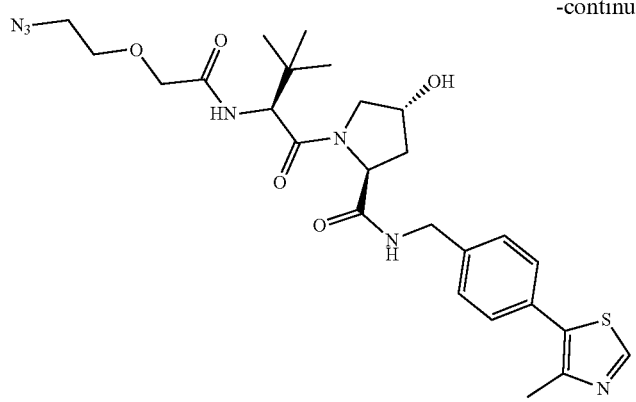

6

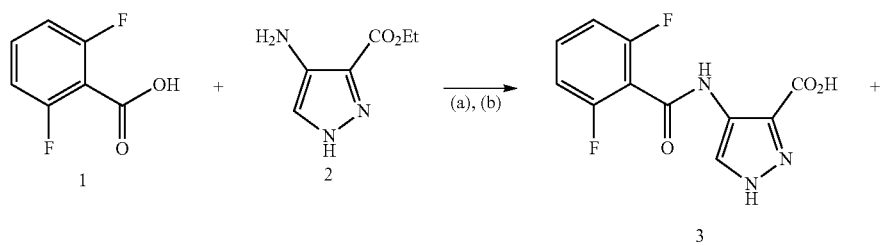

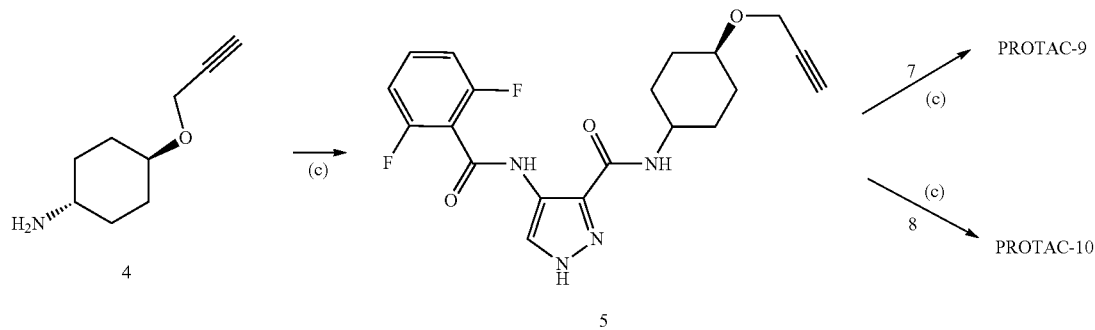

Nuclear Magnetic Resonance (NMR) spectra of 1H and TlPLC analyses to corroborate identity structure and purity are presented in FIGS. 4A-4D and 5.

Example 1

2-(2,6-dioxopiperidin-3-yl)-4-((2-(2-(2-(2-(4-(3-((4-((4-(1-isopropyl-2-methyl-1H-imidazol-5-yl)pyrimidin-2-yl)amino)phenyl)sulfonyl)propyl)-1H-1,2,3-triazol-1-yl)ethoxy)ethoxy)ethoxy)ethyl)amino)isoindoline-1,3-dione (PROTAC-7): To a mixture of 4-(1-isopropyl-2-methyl-1H-imidazol-5-yl)-N-(4-(pent-4-yn-1-ylsulfonyl)phenyl)pyrimidin-2-amine (8 mg) and 4-((2-(2-(2-(2-azidoethoxy)ethoxy)ethoxy)ethyl)amino)-2-(2,6-dioxopiperidin-3-yl)isoindoline-1,3-dione (9 mg) in DMSO (450 μL) and water (300 μL) was added copper sulfate (3.4 mg), followed by a solution of sodium (R)-5-((S)-1,2-dihydroxyethyl)-4-hydroxy-2-oxo-2,5-dihydrofuran-3-olate (8.5 mg) in water (150 μL). The mixture was stirred at rt for 20 h. The mixture was filtered rinsing with a small amount of DMSO (1 mL) and then purified by prep HPLC to give the product as a yellow solid (3.6 mg, 21% yield). $^1$H NMR (500 MHz, Methanol-$d_4$) δ 8.45 (d, J=5.2 Hz, 1H), 8.42 (bs, 1H), 7.96-7.94 (m, 2H), 7.79-7.76 (m, 3H), 7.50 (dd, J=8.5, 7.1 Hz, 1H), 7.43 (s, 1H), 7.13 (d, J=5.2 Hz, 1H), 7.02 (dd, J=14.6, 7.8 Hz, 2H), 5.75 (p, J=7.1 Hz, 1H), 5.02 (dt, J=12.8, 6.3 Hz, 1H), 4.48-4.46 (t, J=5.2 Hz, 2H), 3.82-3.80 (t, J=5.2 Hz, 2H), 3.68 (t, J=5.2 Hz, 2H), 3.62-3.59 (m, 2H), 3.58-3.56 (m, 2H), 3.55 (s, 4H), 3.45 (t, J=5.2 Hz, 2H), 3.23-3.19 (m, 2H), 2.88-2.81 (m, 1H), 2.78-2.74 (m, 2H), 2.71-2.68

(m, 1H), 2.58 (s, 3H), 2.11-1.97 (m, 4H), 1.54 (d, J=7.1 Hz, 6H). HRMS (ESI) m/z calcd for $C_{43}H_{51}N_{11}O_9S$ (M+H)+ 898.3670, found 898.3677.

Example 2

(2S,4R)-4-hydroxy-1-((S)-2-(2-(2-(4-(3-((4-((4-(1-isopropyl-2-methyl-1H-imidazol-5-yl)pyrimidin-2-yl)amino) phenyl)sulfonyl)propyl)-1H-1,2,3-triazol-1-yl)ethoxy)acetamido)-3,3-dimethylbutanoyl)-N-(4-(4-methylthiazol-5-yl) benzyl)pyrrolidine-2-carboxamide (PROTAC-8): To a mixture of 4-(1-isopropyl-2-methyl-1H-imidazol-5-yl)-N-(4-(pent-4-yn-1-ylsulfonyl)phenyl)pyrimidin-2-amine (8 mg) and (2S,4R)-1-((S)-2-(2-(2-azidoethoxy)acetamido)-3,3-dimethylbutanoyl)-4-hydroxy-N-(4-(4-methylthiazol-5-yl)benzyl)pyrrolidine-2-carboxamide (10 mg) in DMSO (450 μL) and water (300 μL) was added copper sulfate (3.2 mg), followed by a solution of sodium (R)-5-((S)-1,2-dihydroxyethyl)-4-hydroxy-2-oxo-2,5-dihydrofuran-3-olate (8 mg) in water (150 μL). The mixture was filtered, rinsing with a small amount of DMSO, and purified by prep HPLC. White solid (5.4 mg, 31% yield). $^1$H NMR (500 MHz, Methanol-$d_4$) δ 8.84 (s, 1H), 8.45 (d, J=5.2 Hz, 1H), 7.96 (d, J=8.8 Hz, 2H), 7.82 (s, 1H), 7.78 (d, J=8.9 Hz, 2H), 7.47-7.41 (m, 3H), 7.39 (d, J=8.4 Hz, 2H), 7.13 (d, J=5.2 Hz, 1H), 5.82-5.67 (m, 1H), 4.67-4.56 (m, 4H), 4.50 (d, J=15.4 Hz, 1H), 4.37 (d, J=15.5 Hz, 1H), 4.07-3.97 (m, 2H), 3.97-3.90 (m, 2H), 3.87-3.75 (m, 2H), 3.23-3.15 (m, 2H), 2.79 (t, J=7.5 Hz, 2H), 2.59 (d, J=3.6 Hz, 3H), 2.44 (s, 3H), 2.28-2.19 (m, 1H), 2.12-1.97 (m, 3H), 1.56-1.52 (m, 6H), 0.98 (s, 9H). HRMS (ESI) m/z calcd for $C_{48}H_{60}N_{12}O_7S_2$ (M+H)$^+$ 981.4228, found 981.4227.

Example 3

4-(2,6-difluorobenzamido)-N-((1r,4r)-4-((1-(2-(2-(2-(2-((2-(2,6-dioxopiperidin-3-yl)-1,3-dioxoisoindolin-4-yl) amino)ethoxy)ethoxy)ethoxy)ethyl)-1H-1,2,3-triazol-4-yl) methoxy)cyclohexyl)-1H-pyrazole-3-carboxamide (PROTAC-9): To a mixture of 4-(2,6-difluorobenzamido)-N-((1r,4r)-4-(prop-2-yn-1-yloxy)cyclohexyl)-1H-pyrazole-3-carboxamide (8 mg) and 4-((2-(2-(2-(2-azidoethoxy) ethoxy)ethoxy)ethyl)amino)-2-(2,6-dioxopiperidin-3-yl) isoindoline-1,3-dione (10.4 mg) in DMSO (450 μL) and water (300 μL) was added copper sulfate (3.6 mg), followed by a solution of sodium (R)-5-((S)-1,2-dihydroxyethyl)-4-hydroxy-2-oxo-2,5-dihydrofuran-3-olate (8.9 mg) in water (150 μL). The mixture was stirred at rt for 20 h. Water (5 mL) was added and the mixture was extracted with EtOAc (3×5 mL). The organics were dried over Na$_2$SO$_4$, filtered, and concentrated. Flash chromatography (CH$_2$Cl$_2$:MeOH (0 to 10%)) gave the title compound as a yellow solid (5 mg, 29%). $^1$H NMR (400 MHz, Methanol-$d_4$) δ 8.33 (s, 1H), 7.99 (s, 1H), 7.61-7.46 (m, 2H), 7.16-7.10 (m, 2H), 7.05 (dd, J=13.3, 7.8 Hz, 2H), 5.03 (dd, J=12.4, 5.5 Hz, 1H), 4.60 (s, 2H), 4.57-4.51 (m, 2H), 3.88-3.83 (m, 2H), 3.71 (t, J=5.2 Hz, 2H), 3.66-3.60 (m, 4H), 3.59 (s, 4H), 3.48 (t, J=5.2 Hz, 2H), 3.43 (dd, J=9.7, 5.4 Hz, 1H), 2.92-2.78 (m, 1H), 2.78-2.62 (m, 2H), 2.11-2.07 (m, 2H), 1.96 (s, 2H), 1.48-1.27 (m, 6H). HRMS (ESI) m/z calcd for $C_{41}H_{46}F_2N_{10}O_{10}$ (M+H)$^+$ 877.3445, found 877.3444.

Example 4

4-(2,6-difluorobenzamido)-N-((1S,4r)-4-((1-(2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-2-oxoethoxy)ethyl)-1H-1,2,3-triazol-4-yl)methoxy) cyclohexyl)-1H-pyrazole-3-carboxamide (PROTAC-10): To a mixture of 4-(2,6-difluorobenzamido)-N-((1r,4r)-4-(prop-2-yn-1-yloxy)cyclohexyl)-1H-pyrazole-3-carboxamide (8 mg) and (2S,4R)-1-((S)-2-(2-(2-azidoethoxy)acetamido)-3,3-dimethylbutanoyl)-4-hydroxy-N-(4-(4-methylthiazol-5-yl)benzyl)pyrrolidine-2-carboxamide (10 mg) in DMSO (450 μL) and water (300 μL) was added copper sulfate (3.2 mg), followed by a solution of sodium (R)-5-((S)-1,2-dihydroxyethyl)-4-hydroxy-2-oxo-2,5-dihydrofuran-3-olate (8 mg) in water (150 μL). The mixture was diluted with EtOAc (10 mL) and water (10 mL) and the layers were separated. The aqueous layer was extracted with EtOAc (3×10 mL). The combined organics were washed with brine (10 mL), dried over Na$_2$SO$_4$, filtered, and concentrated. Flash chromatography in CH$_2$Cl$_2$/MeOH (1-12%) provided the desired product as colorless oil (4.1 mg, 24% yield). $^1$H NMR (500 MHz, Methanol-$d_4$) δ 8.87 (s, 1H), 8.33 (s, 1H), 8.05 (s, 1H), 7.57 (tt, J=8.4, 6.3 Hz, 1H), 7.48-7.40 (m, 4H), 7.13 (t, J=8.4 Hz, 2H), 4.70-4.61 (m, 5H), 4.61-4.47 (m, 3H), 4.37 (d, J=15.4 Hz, 1H), 4.07-3.99 (m, 2H), 3.99-3.94 (m, 2H), 3.88-3.77 (m, 3H), 3.47-3.40 (m, 1H), 2.47 (s, 3H), 2.26-2.18 (m, 1H), 2.14-2.01 (m, 4H), 1.96 (d, J=12.8 Hz, 1H), 1.44-1.35 (m, 4H), 1.01 (s, 9H). HIRMS (ESI) m/z calcd for $C_{46}H_{55}F_2N_{11}O_8S$ (M+H)$^+$ 960.4002, found 960.4002.

Examples 5 and 6

AZD5438 was identified as a lead compound from the high-throughput screening of a library of 187 CDK2 inhibitors, performed in an inner ear cell line (HEI-OC1). AZD5438 is a potent CDK2 inhibitor tested in solid-tumor therapy and has completed a phase 2 clinical trial. It has been also demonstrated that AZD5438 fully protects against cisplatin-induce hearing loss in mice by local delivery. This compound is the most potent CDK2 inhibitor that shows protection against cisplatin toxicity in cochlear explants that we have identified so far (IC$_{50}$=5 nM, therapeutic index >200). It exhibits protection against cisplatin-induced hair cell loss around 1,000-times better than four other benchmark compounds (sodium thiosulfate, Ebselen, D-methionine, and Dexamethasone) in clinical trials for hearing loss under identical cochlear explant assay conditions. ACD5438 protects zebrafish lateral line against cisplatin ototoxicity. Since fish and mammalian hair cells are equally susceptible to ototoxic insults, any potential compound exerting an otoprotective effect in fish hair cells is likely to have a similar effect on mammals.

Scheme 3 shows a multi-step synthetic scheme for Examples 5 and 6, as well as Examples 1 and 2. Reaction conditions: (a) DMF, rt, 36 h; (b) NaOtBu (3.0 equiv.), BINAP (0.1 equiv), Pd$_2$(dba)$_3$ (0.5 equiv), 1,4-dioxane, 80° C., 2 h; (c) CuSO$_4$ (1.1 equiv.), sodium ascorbate (2.2 equiv.), DMSO: H$_2$O (1:1), rt, 20 h; (d) 2-(2-(2-azidoethoxy) ethoxy)ethanamine (1.0 equiv.), DIPEA (2.0 equiv.), DMF, 90° C., 18 h; (3) 2-(2-azidoethoxy)acetic acid (1.0 equiv.), DIPEA (6.0 equiv), HATU (4.0 equiv), DMF, 0° C.-rt, 20 min.

Scheme 3. Multi-step synthetic scheme for Examples 1, 2, 5, and 6.
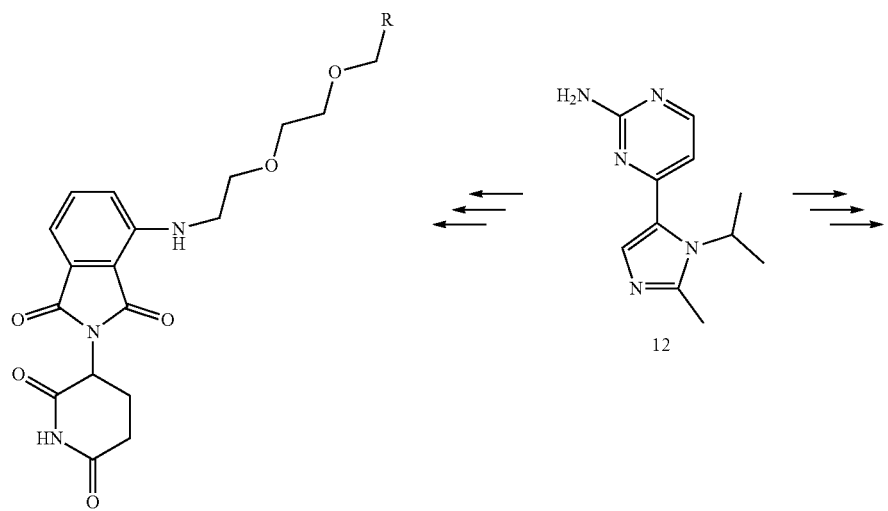
Ex. 1 and 6
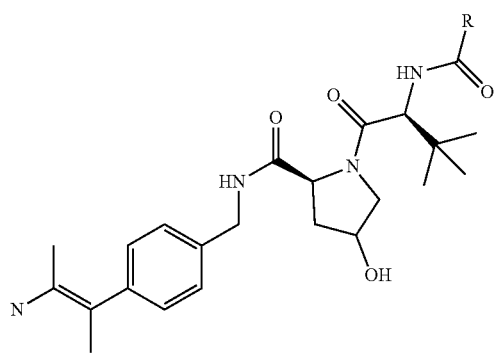
Ex. 2 and 5
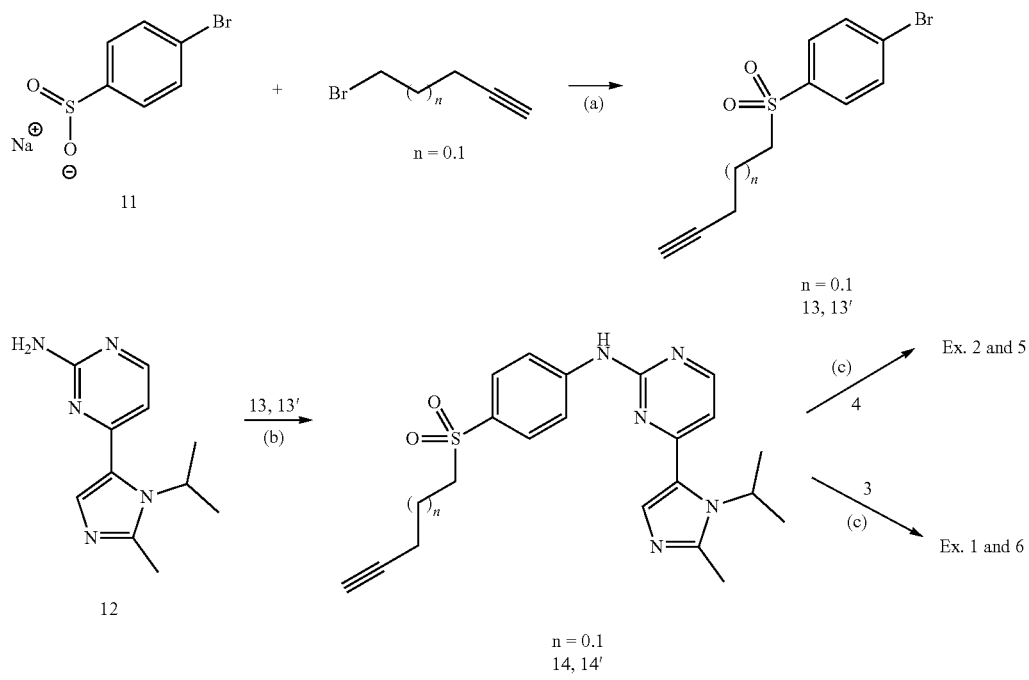

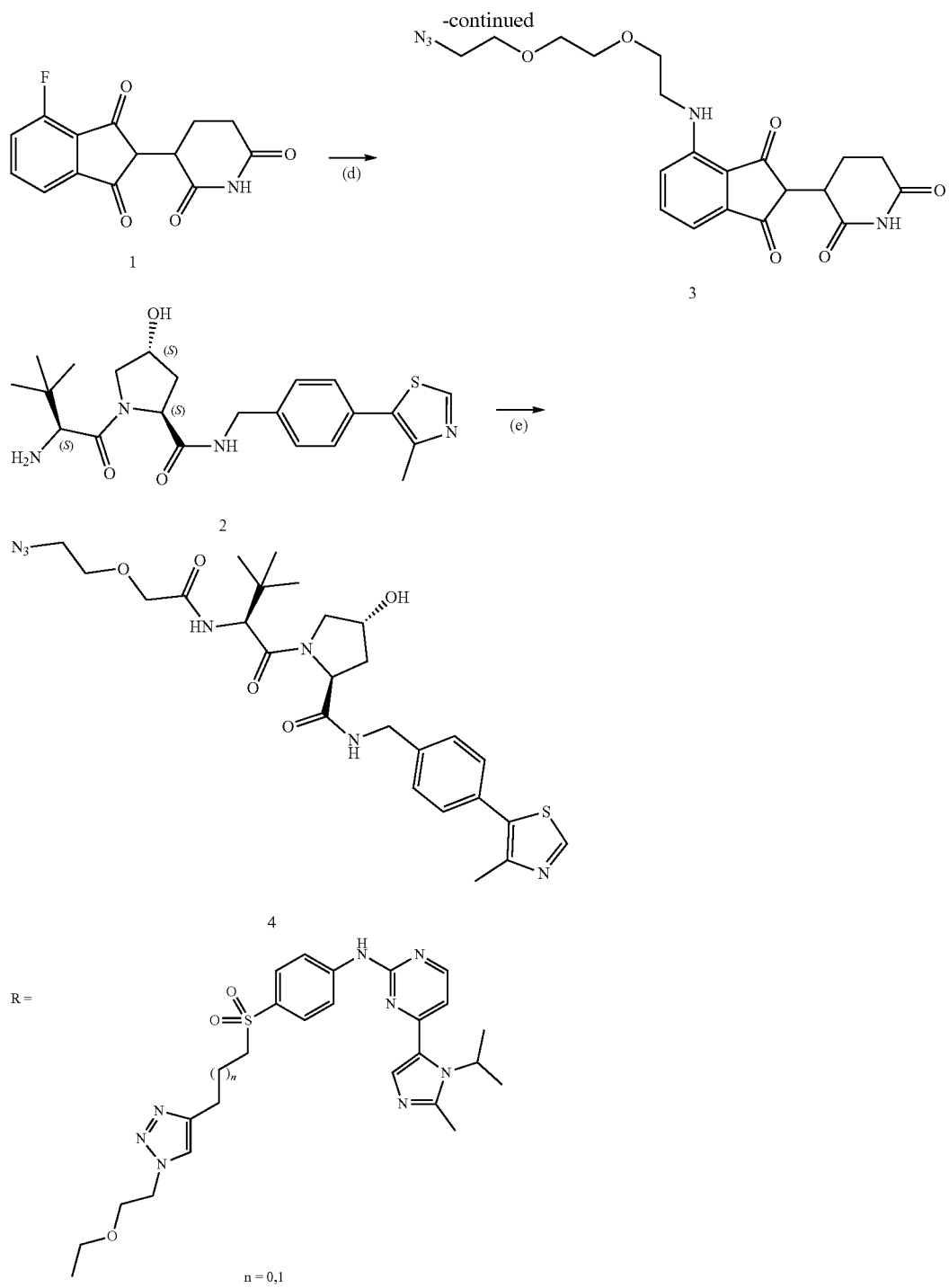

To synthesize the linker containing the E3 ligase, we used 2-(2-(2-azidoethoxy)ethoxy)ethanamine (reaction condition d) and 2-(2-azidoethoxy)acetic acid (reaction condition e) to couple with CRBN (1) and VHL (2) ligands respectively to yield respective azide 3 and 4. Final compounds were prepared using click chemistry approach in presence of the corresponding azide at room temperature. Briefly, sodium 4-bromobenzenesulfinate (11) was added in homopropargyl bromide or 6-Bromohex-1-hyne to form compound 13 or 13' (reaction condition a). Coupling of compound 13 or 13' with the 4-(1-isopropyl-2-methyl-1H-imidazol-5-yl)pyrimidin-2-amine (12) in presence of catalyst and base produced respective alkyne 14 or 14' (reaction condition b). Addition of compound 14 or 14' with the respective azide 3 and 4 (reaction condition c) yielded AZD5438 linked PROTAC compounds of Examples 1, 2, 5, and 6. For Examples 1 and 2, n=1 and for Examples 5 and 6, n=0.

CDK2 Degradation in HEI-OC1 Cells

Figure 4A:
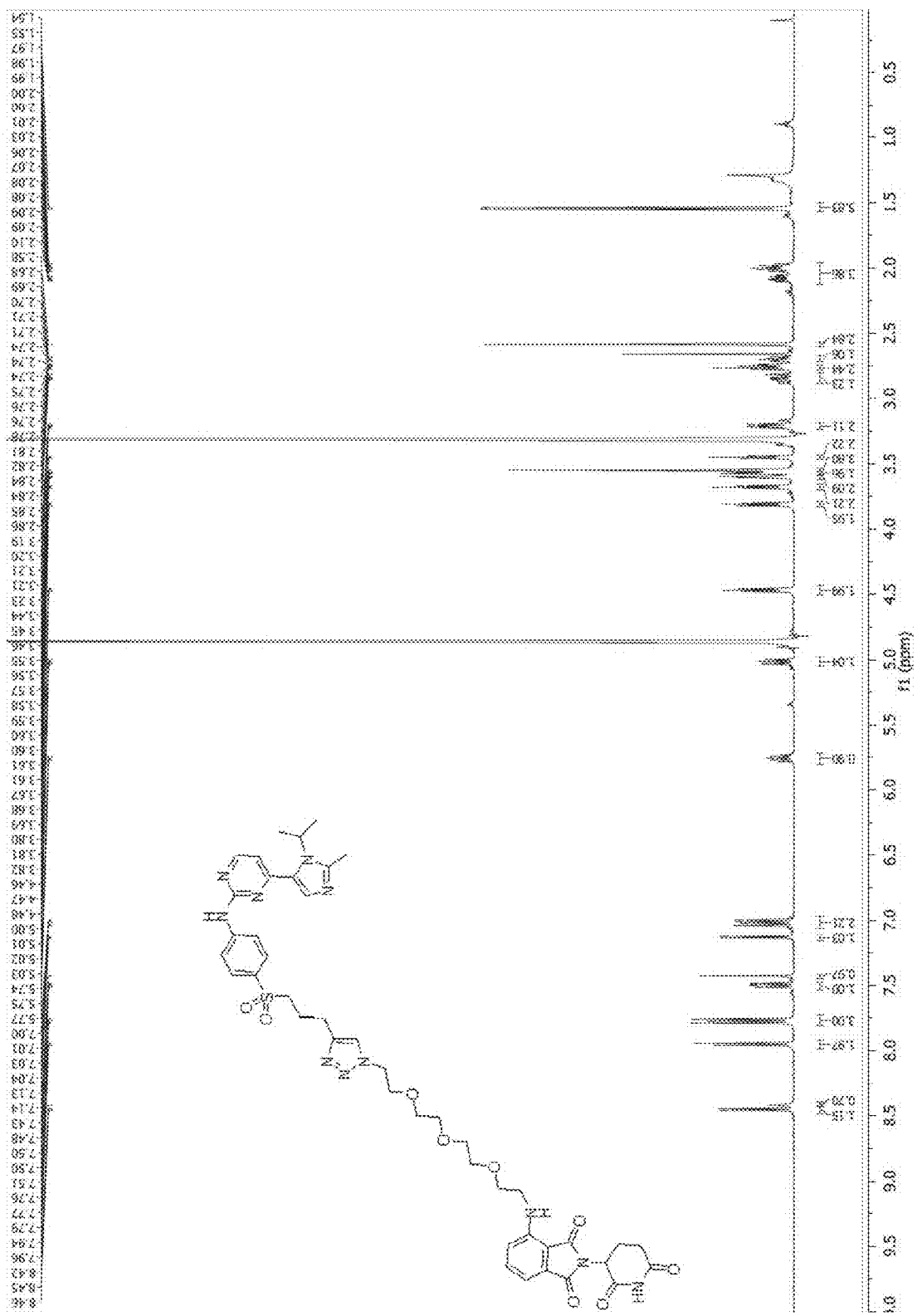
FIGS. 4A-4D show 1H NMR Spectra of compounds of Formula (1)
Figure 4B:
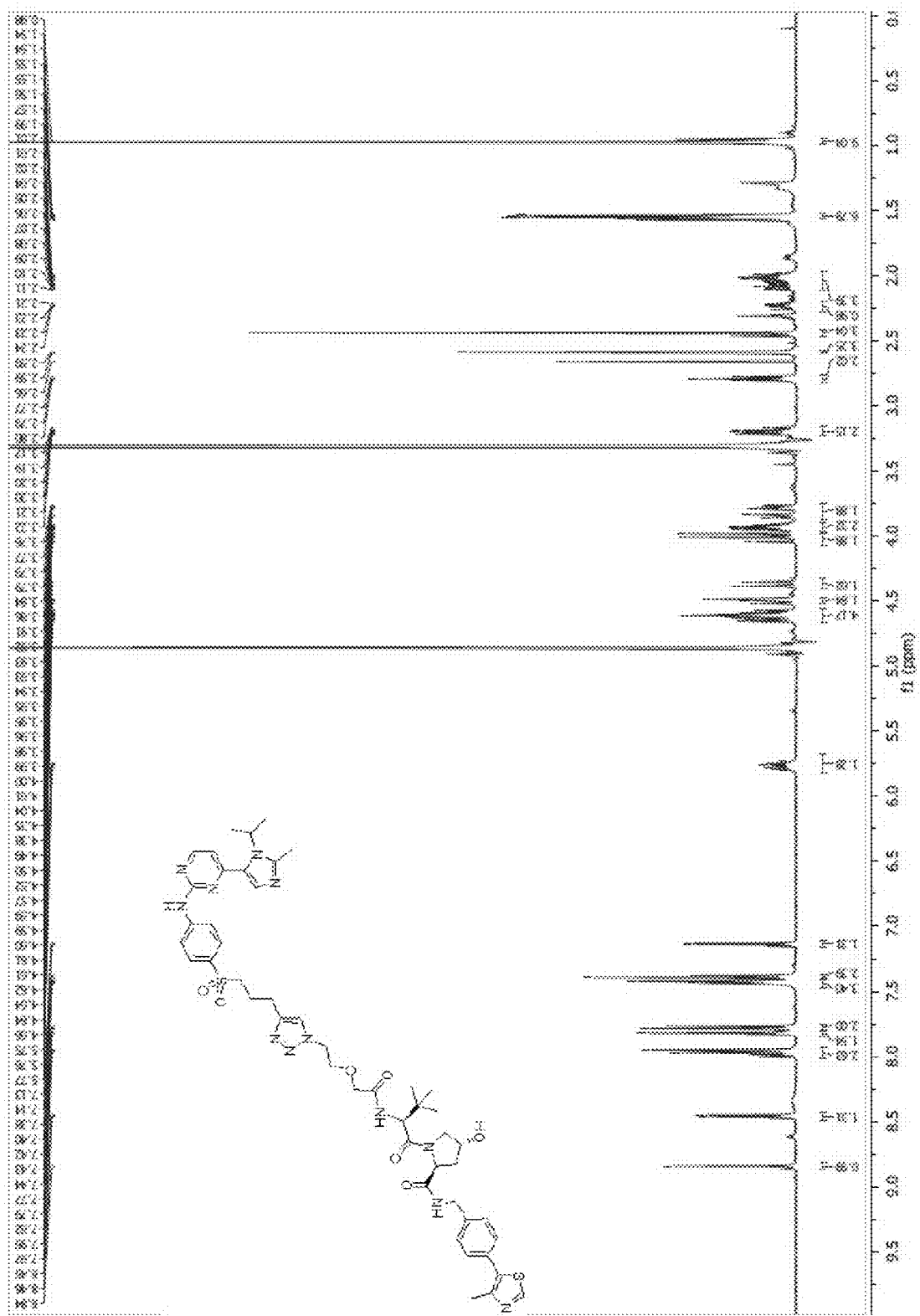
Figure 4C:
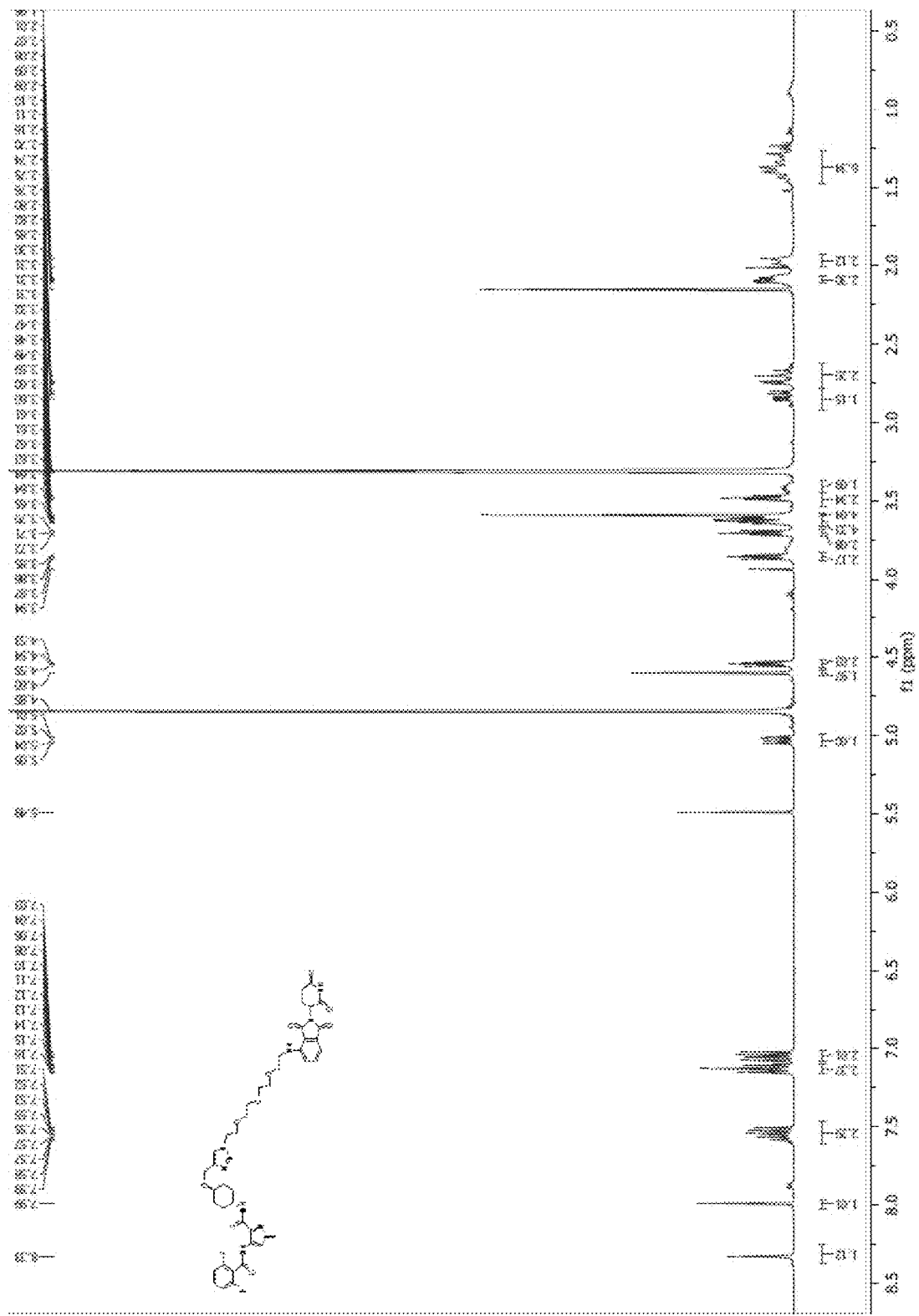
Figure 4D:
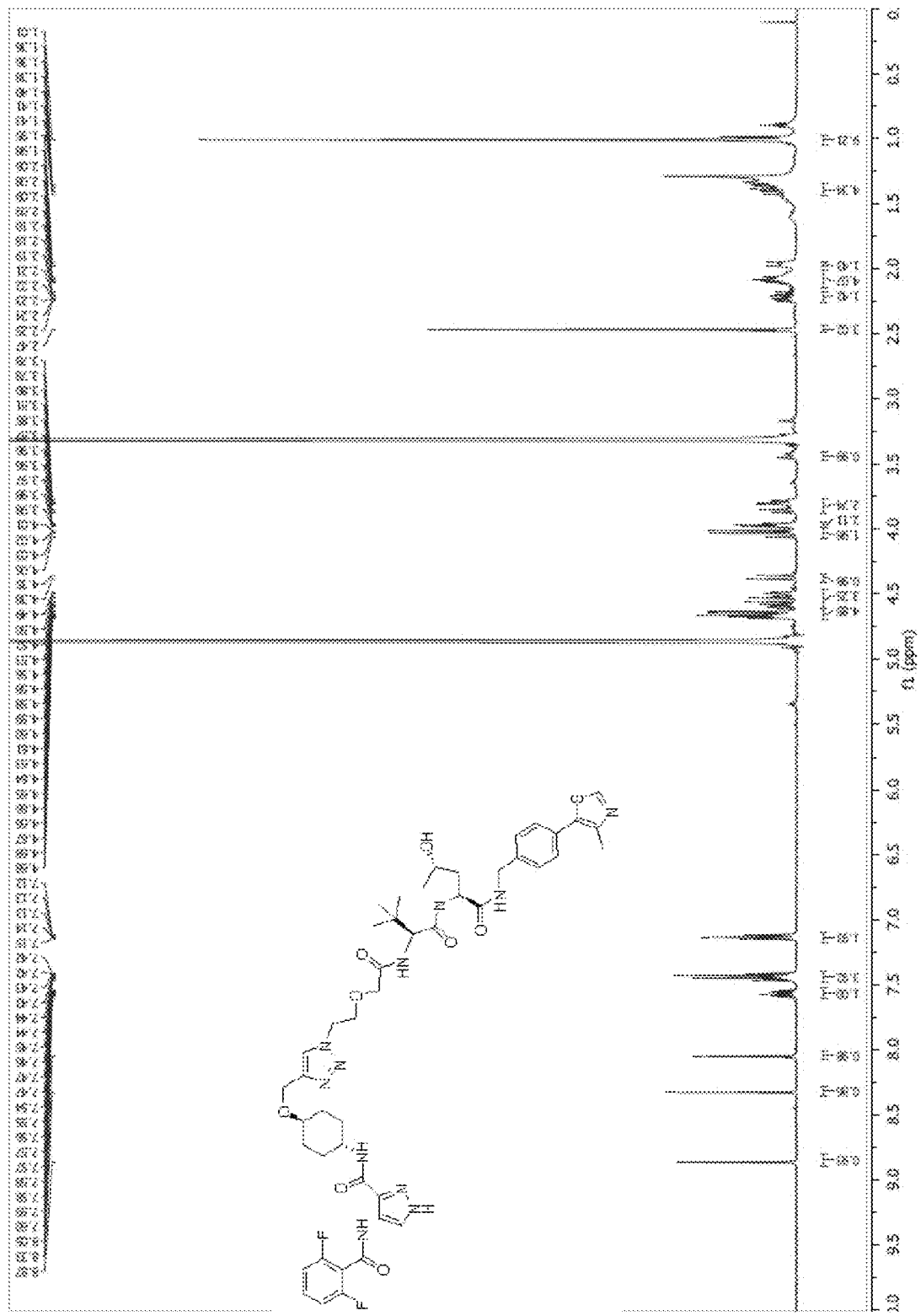
Figure 5:
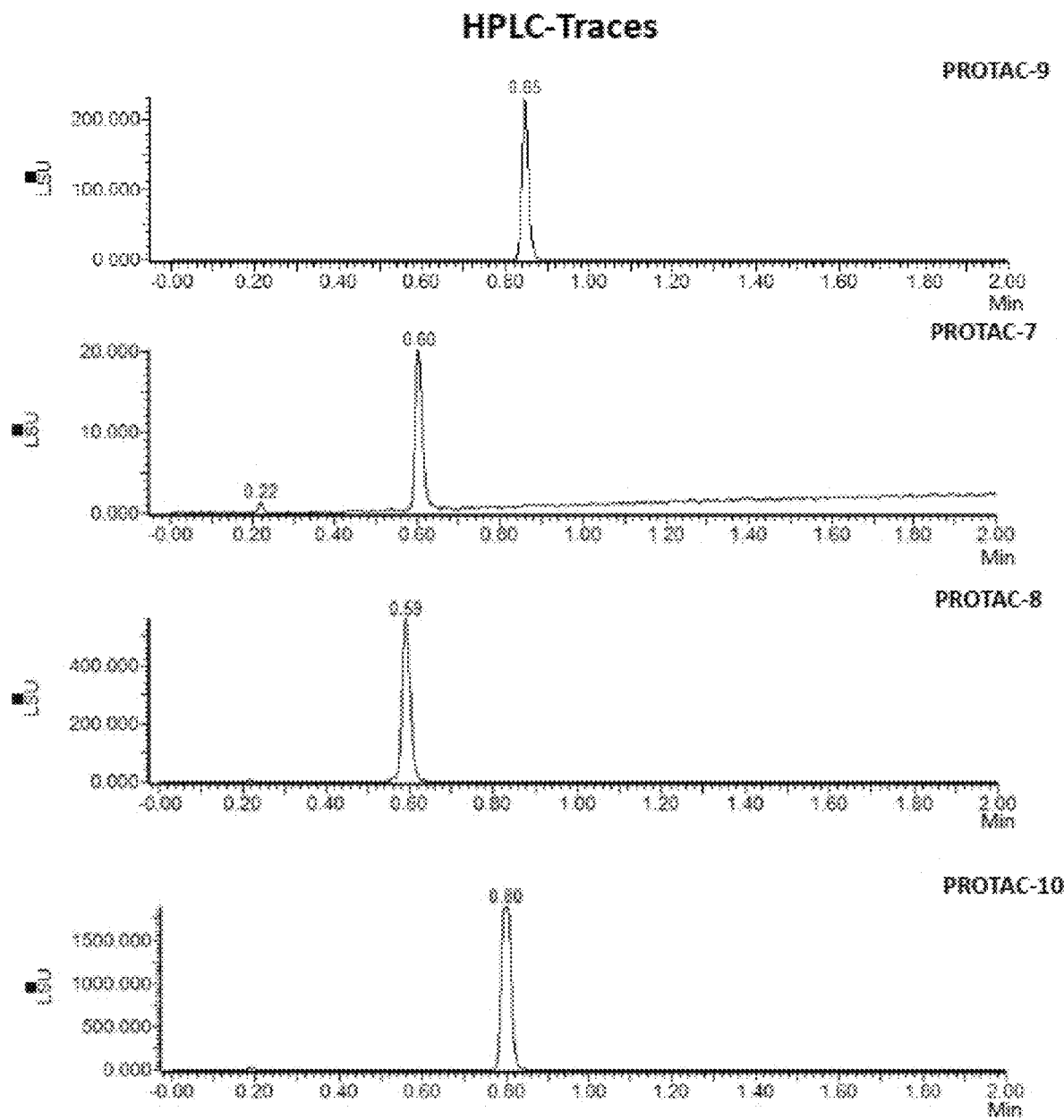
FIG. 5 shows HPLC traces of the compounds of Examples 1-4.

The synthesized PROTACs of Examples 1-4 were screened for CDK2 degradation in HEI-OC1 cells incubated for 24 hours with a wide range of concentrations, from 0.1 nM to 1 μM (FIGS. 6A-6D). We also included the two CDK2 ligands used in the PROTAC design, AZD5438 and AT7519-7. From the initial screening, AZD5438-linked PROTAC with VH-032 as E3 ligase ligand, (Example 2), induced around 50% CDK2 degradation at 100 nM concentration (FIG. 6C) while AZD5438 alone had no significant effect on the degradation. Treatment of HEI-OC1 cells with AT7519-7-linked PROTACs, i.e., Example 3 and Example 4, or AZD5438-PROTAC with the CRBN ligand, Example 1, did not show any CDK2 degradation (FIG. 6A), nor changes in the abundance of any of the closely related CDKs (FIGS. 4A-4C).

Figures 6A, 6B, 6C, 6D:
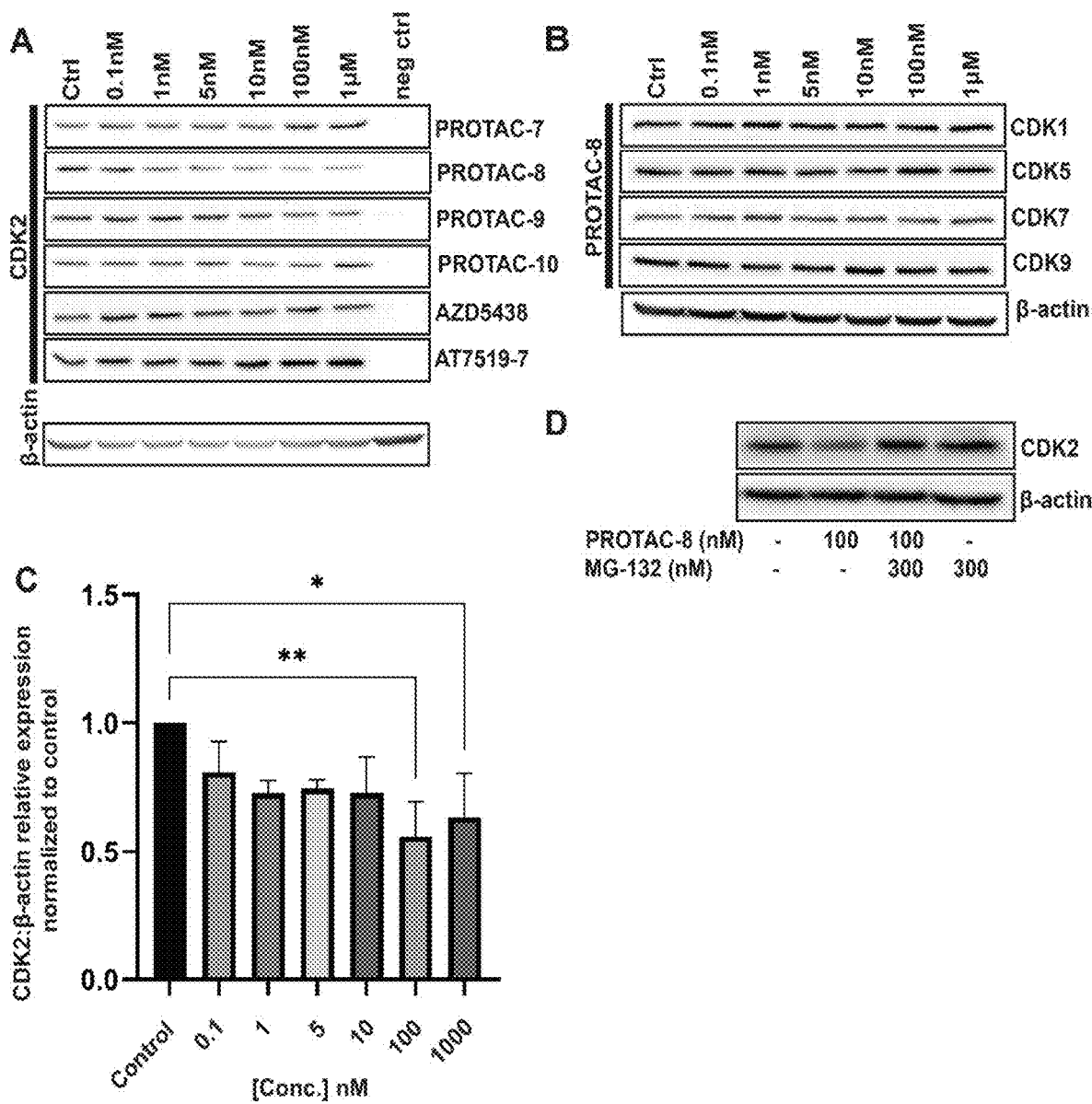
FIGS. 6A-6D show the evaluation of the compounds of Examples 1-4 treatment results in CDK2 degradation.

PROTAC-8 was tested to determine whether the compound degrades CDK1, CDK5, CDK7 or CDK9, and observed that the compound of Example 2 was selective for CDK2 degradation (FIG. 6B-6C), with a half maximal degradation concentration ($DC_{50}$) of >1 µM. PROTAC-8's degradation effect was through the proteasomal pathway, since co-incubation of the HEI-OC1 cells with 100 nM of PROTAC-8 and 300 nM of the proteasome inhibitor, MG-132, abolished CDK2 degradation (FIG. 6D).

Structure of the Complex

Figures 7A, 7B, 7C:
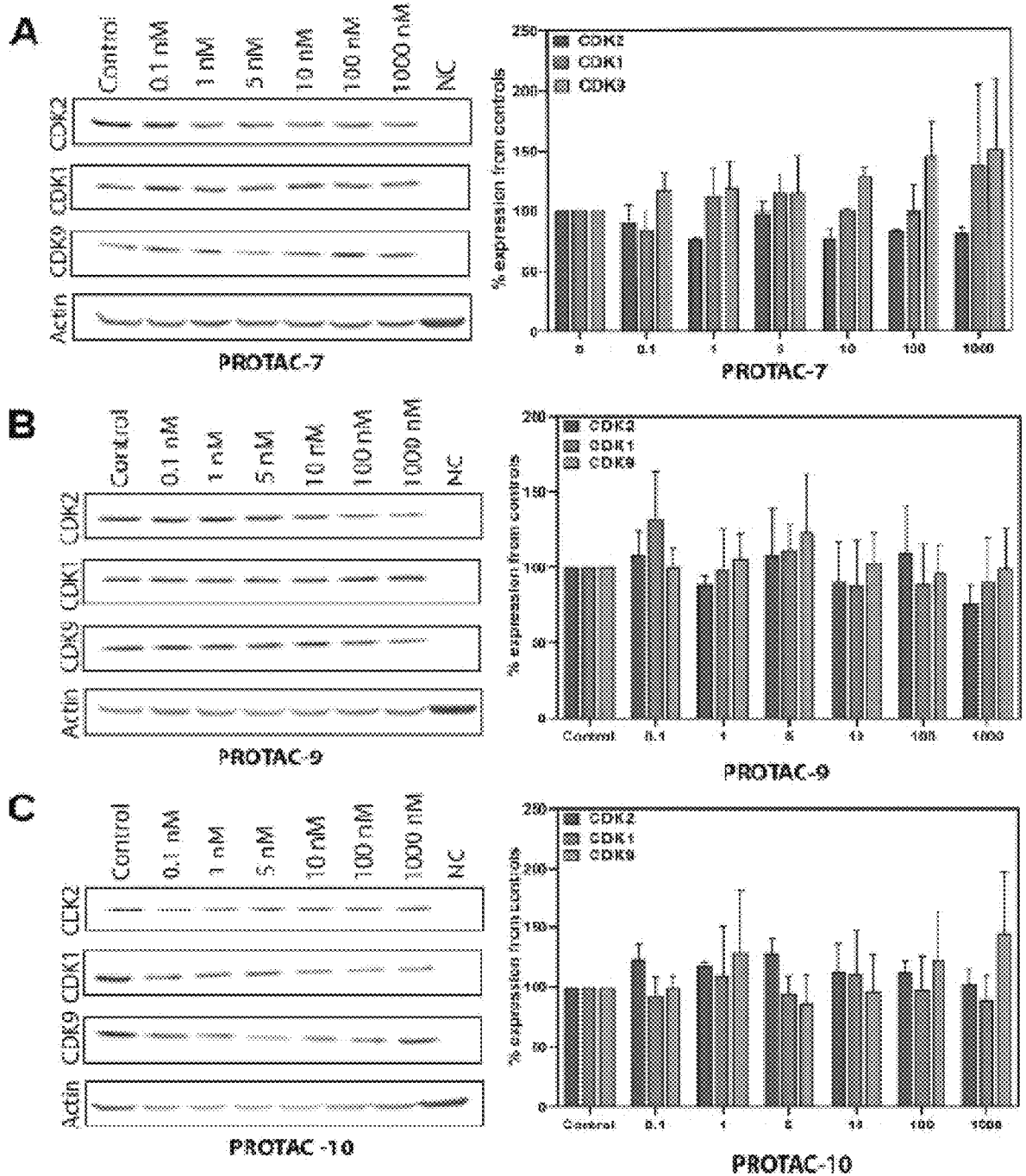
FIGS. 7A-7C show characterization of PROTACs in HEI-OC1 cells. HEI-OC1 cells were incubated for 24 hours with different concentrations of the compound of Example 1 (FIG. 7A); the compound of Example 2 (FIG. 7B); and the compound of Example 4 (FIG. 7C). Cells were harvested and processed for immunoblot detection of CDK2, CDK1, and CDK9. Left: Representative immunblots. Right: Quantification analysis of the specific bands for CDK2, CDK1, and CDK9 from two independent experiments. Results were expressed as mean+/−SEM. Actin was used as a loading control. NC: Kidney lysate from CDK2 knockout mouse used as a negative control for CDK2 immunodetection.
Figures 8A, 8B:
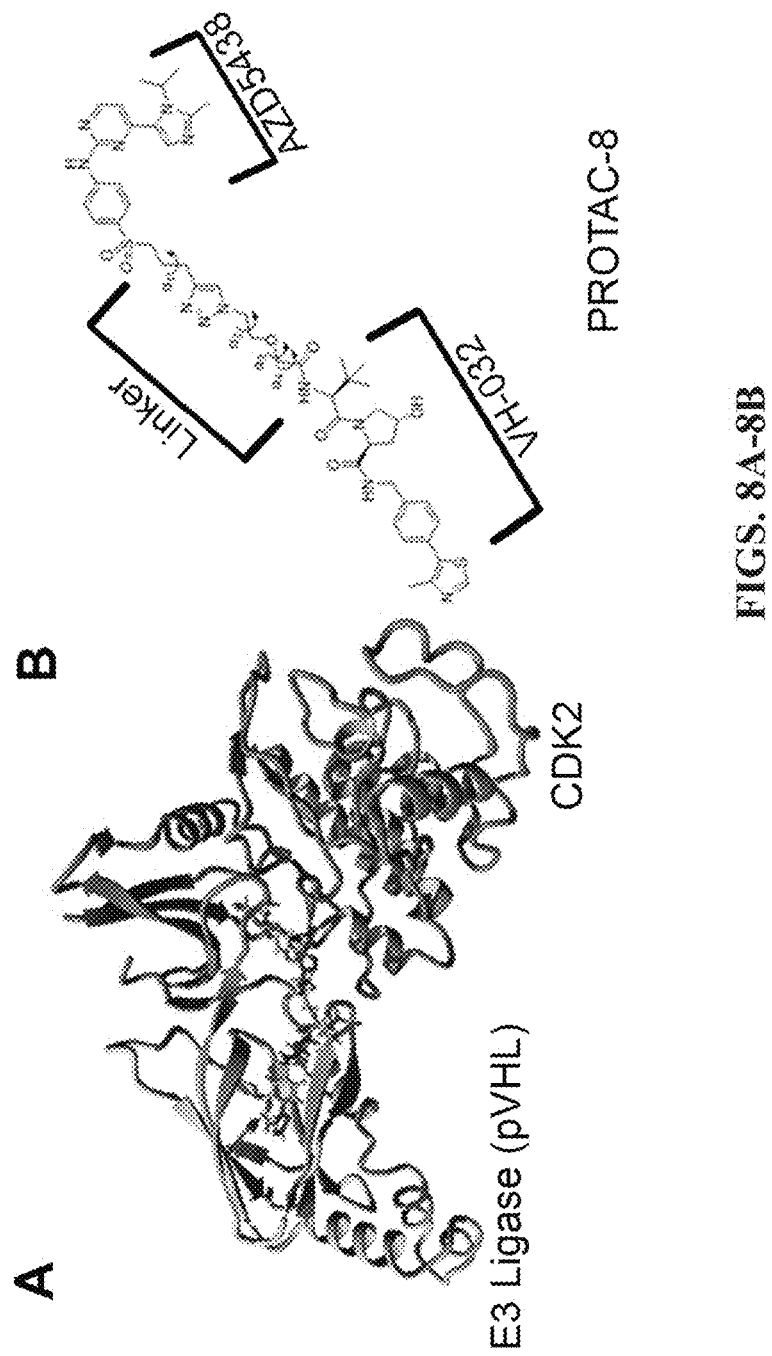
FIGS. 8A-8B show a structure of pVHL-PROTAC-8-CDK2 ternary complex.
Figures 9A, 9B:
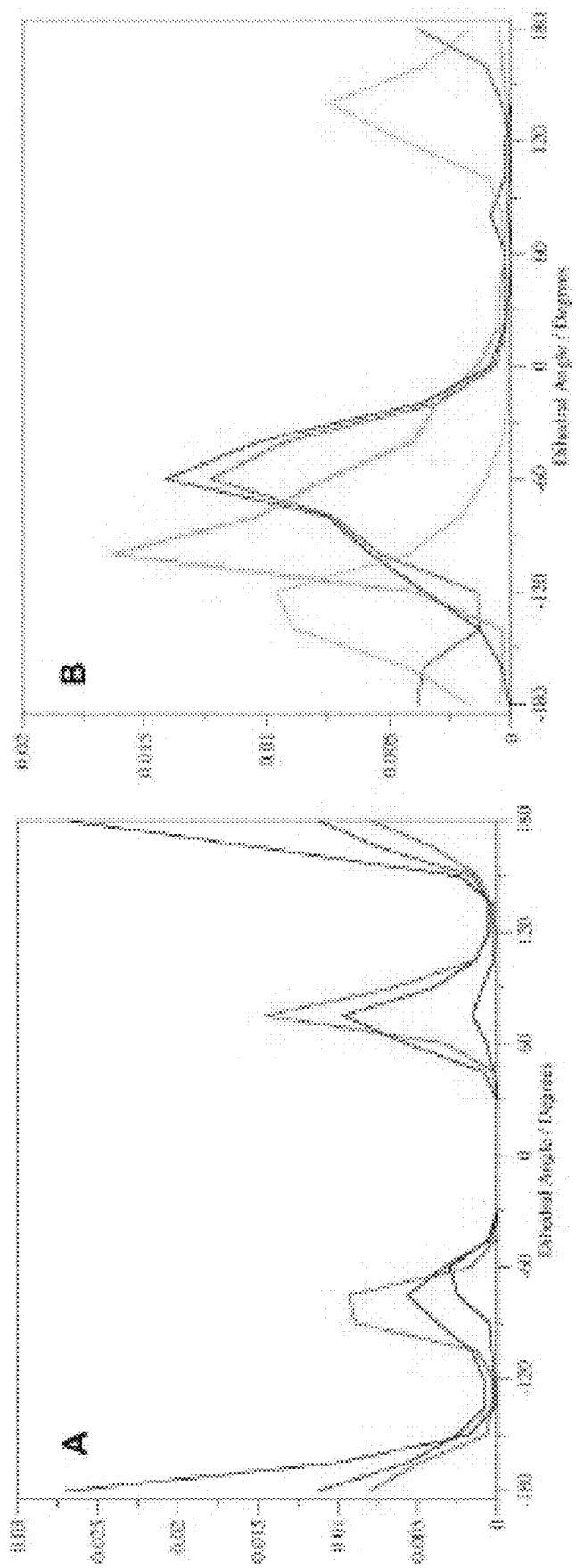
FIGS. 9A-9B show the distribution of α1, α2, α3, and α4 dihedral angles during Molecular Dynamics (MD) simulations.
Figure 10A:
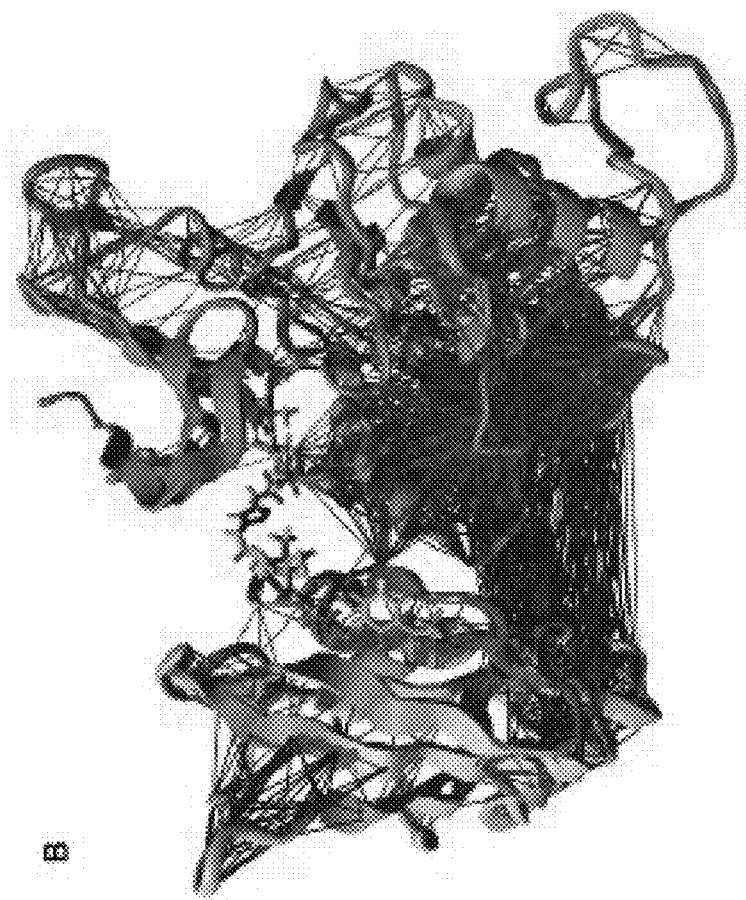
FIGS. 10A-10B show dynamic cross-correlation matrix (DCCM) analysis of trajectories. pVHL (grey) connected through PROTAC-8 to CDK2 (orange), red and blue lines are shown between correlated and anti-correlated Ca atom pairs, respectively.
Figure 10B:
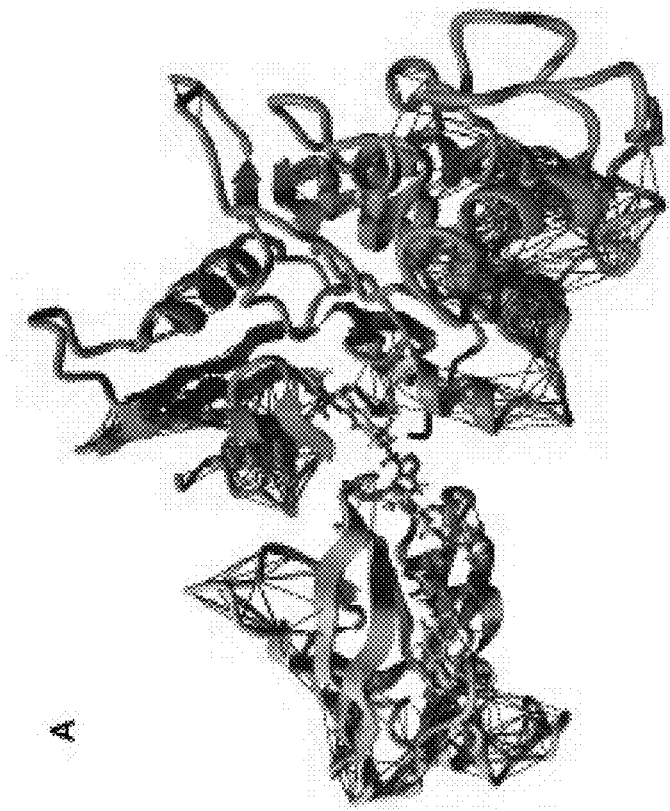
Figures 11A, 11B, 11C:
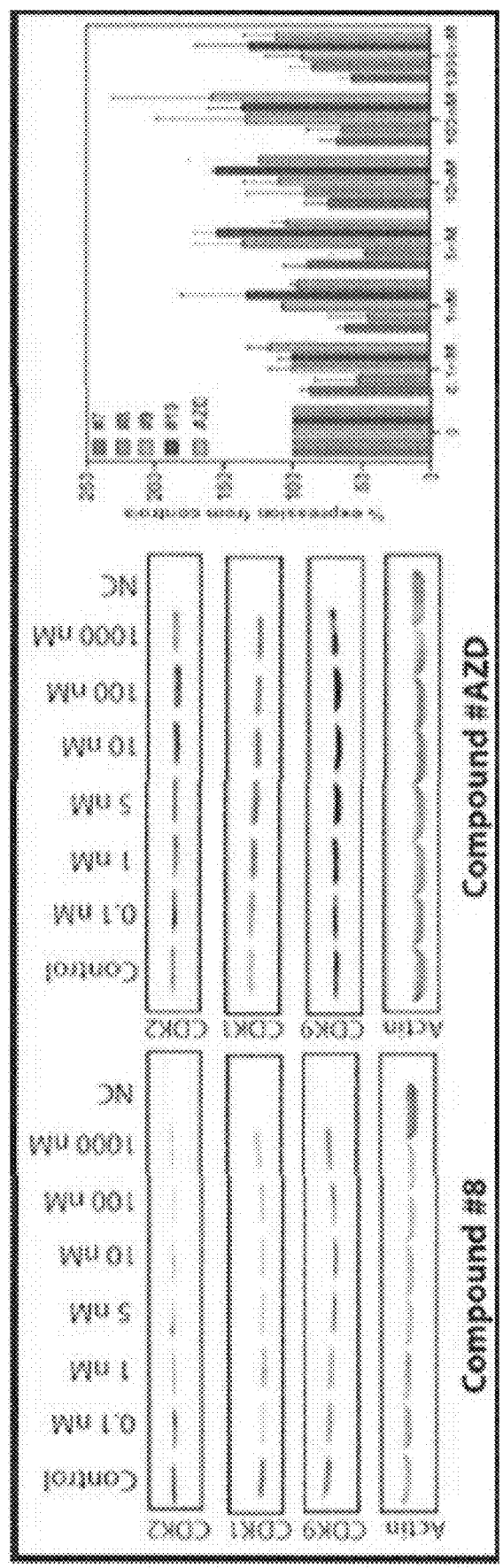
FIGS. 11A-11C show that PROTAC-8 protects zebrafish hair cells from cisplatin otoxicity.

The structure and dynamics of the ternary complex formed by the association of the E3 ligase, PROTAC-8, and CDK2 (pVHL-PROTAC-8-CDK2) were studied by five 10 ns independent molecular dynamics (MD) simulations using the AMBERff14SB force field as implemented in the YASARA package (FIG. 8A). (Maier, J. A.; Martinez, C.; Kasavajhala, K.; Wickstrom, L.; Hauser, K. E.; Simmerling, C., ff14SB: Improving the Accuracy of Protein Side Chain and Backbone Parameters from ff99SB. *J. Chem. Theory. Comput.* 2015, 11, 3696-3713; Krieger, E.; Vriend, G., New ways to boost molecular dynamics simulations. *J. Comput. Chem.* 2015, 36, 996-1007.) During simulations, both CDK2 and pVHL retained their X-ray structure and the complexes did not dissociate in either trajectory. The relative movement of the two proteins was analyzed by calculating the bond rotation around $\alpha 1$, $\alpha 2$, $\alpha 3$, and $\alpha 4$ dihedral angles using the GROMACS analysis suite (FIG. 8B). (Abraham, M. J.; Murtola, T.; Schulz, R.; Pilla, S.; Smith, J. C.; Hess, B.; Lindahl, E., GROMACS: High performance molecular simulations through multi-level parallelism from laptops to supercomputers. *SoftwareX* 2015, 1, 19-25.) In all five MD simulations, $\alpha 1$, $\alpha 2$, and $\alpha 3$ showed high flexibility by interchanging between trans, gauche(+) and gauche(−) conformations and they had similar distribution (FIG. 9A). The flexibility of the linker present in the PROTAC-8 molecule provided an independent movement of pVHL about CDK2. In contrast, in the case of the $\alpha 4$ dihedral angle, the rotation about the bond that connects the linker to VH-032, was rigid and stayed in gauche(−) conformation in four simulations (FIG. 9B). This rigidity most likely contributes to the stable binding between the E3 ligase pVHL and its ligand, VH-032, present in PROTAC-8. The independent movement of the two proteins docked to PROTAC-8 is further supported by the dynamic cross-correlation matrix (DCCM) analysis[50, 52] of the MD simulations (FIGS. 7A-7C). (Krieger, E.; Vriend, G., New ways to boost molecular dynamics simulations. *J. Comput. Chem.* 2015, 36, 996-1007; Hunenberger, P. H.; Mark, A. E.; van Gunsteren, W. F., Fluctuation and cross-correlation analysis of protein motions observed in nanosecond molecular dynamics simulations. *J. Mol. Biol.* 1995, 252, 492-503.) In MD simulations 1-4, no correlated movement was observed between pVHL and CDK2 (FIG. 10A), only intradomain correlated movements were observed as indicated by the red lines between Cα atom pairs within each protein. On the contrary, in MD simulation 5 beyond the intradomain correlated movements, the two proteins moved in an anti-correlated manner as indicated by the blue lines between Cα atom pairs between the two proteins (FIG. 10B). This anti-correlated movement coincided with gauche(+) conformation of $\alpha 4$ angle and indicates that such conformation is most likely not advantageous for CDK2 ubiquitination. The independent, noncorrelated movement of the protein provides the opportunity for pVHL to reach various ubiquitination sites on CDK2. Such MD simulation analysis also provides a framework for future design of optimized PROTACs specific for CDK2.

CDK2 Degradation in vivo

Trial 1

Figures 12A, 12B, 12C, 12D, 12E:
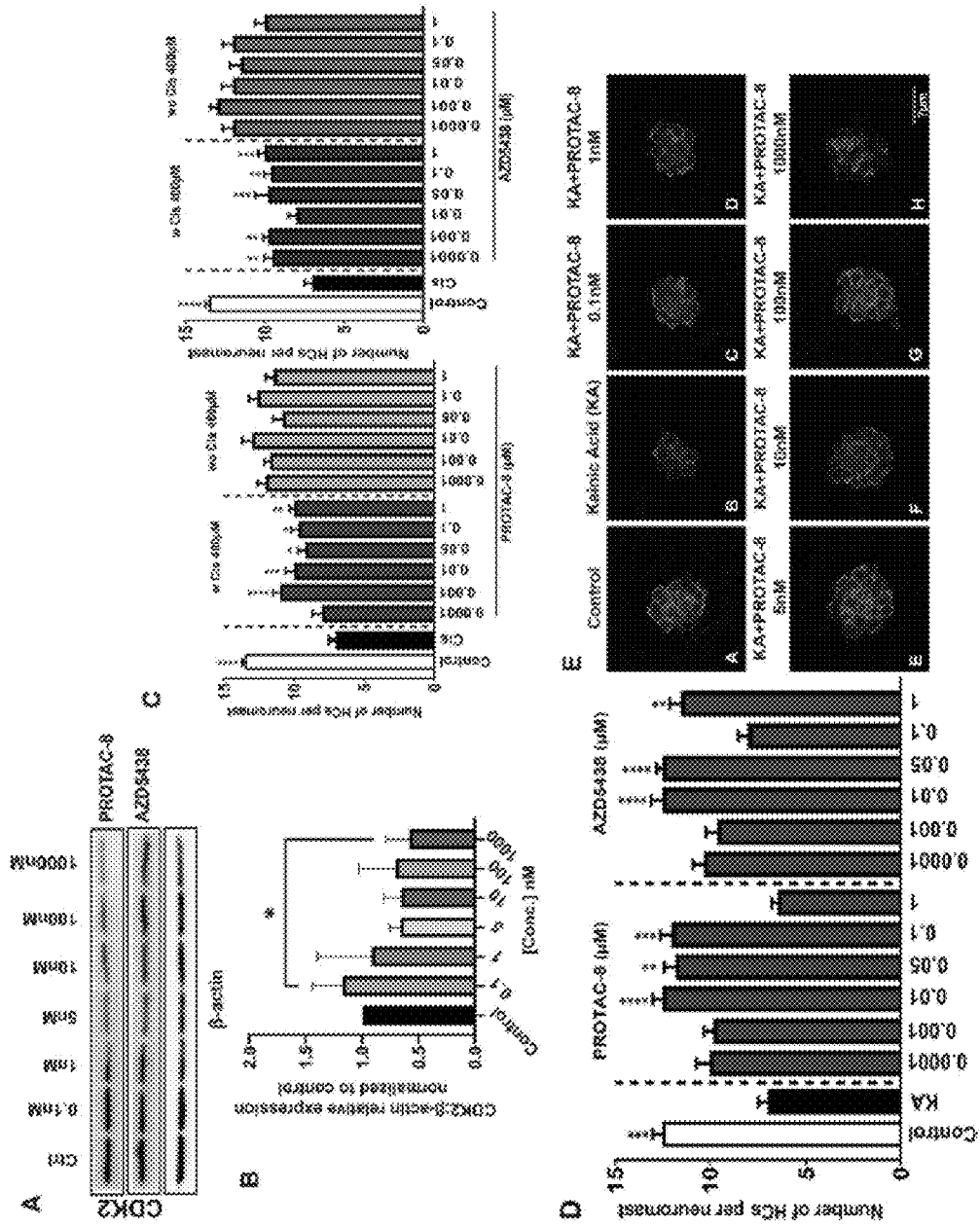
FIGS. 12A-12E shows in vivo evaluation of PROTAC-8.

Further to find the effect of AZD5438-PROTAC 8 (Example 2) in protecting zebrafish hair cells from cisplatin otoxicity, zebrafish were pre-incubated with AZD5438-PROTAC 8 and then co-incubated with cisplatin for six hours. Zebrafish lateral line hair cells were counted and compared with and without PROTAC-8 (FIGS. 12A-12C) which shows that AZD5438-PROTAC 8 significantly protects the zebrafish lateral line neuromasts from cisplatin toxicity (FIG. 12A). To check the degradation of CDK2 in zebrafish, fish were treated with AZD5438-PROTAC 8 in different concentration and total zebrafish lysates used for immunoblots (FIG. 12B). AZD5438-PROTAC 8 degrades CDK2 at concentrations of 0.1 nM and 1 µM (FIGS. 12B-12C). Experiments with AZD5438 were run in parallel and used as controls for hair cell protection without CDK2 degradation.

Trial 2

PROTAC-8 treatment protected neuromast hair cells from kainic acid-induced ototoxicity (FIGS. 12D-12E), showing significant protection at doses doses ranging from 5 nM to 100 nM.

Overall, both AZD5438 and PROTAC-8 were able to protect the zebrafish lateral line neuromasts from cisplatin and kainic acid damage. While inhibition of CDK2 by AZD5438 might contribute to the protective effect observed with PROTAC-8, the specific degradation of CDK2 by PROTAC-8 provides a significant advantage over AZD5438 against cisplatin- and noise-induced hearing loss.

CDK2 Degradation in HeLa Cell Line

To test the efficacy of the synthesized AZD5438-PROTACs, HeLa cells were incubated overnight with different concentrations of AZD5438-PROTAC Examples 1, 2, 5, and 6. Immunoblot experiments showed that only the treatment with AZD5438-PROTAC-8 resulted in the degradation of CDK2. No significant degradation was observed for CDK1 and CDK9 in the presence of AZD5438-PROTAC 2.

Prophetic Examples

Synthesis of a Library of CDK2-PROTACs

To fulfill the potential of targeted protein degradation, a general methodology for an efficient PROTAC design would be desirable. However, the development of active PROTAC degraders is often a laborious and unguided process. The choice of E3 ligase and the selection of target ligands and their conjugation are all potential optimization variables that expand the chemical space to be exploited by medicinal chemists. Properties of the linker, such as length, composition, and site of attachment, are known to be important but often their impact on activity vary in a target- and context-dependent fashion. Moreover, small-molecule binders for both the protein of interest and the E3 ligase are required. Despite the large number of human E3 ubiquitin ligases potulated to function in cells, only a few have good quality ligands that have been successfully used for PROTACs. The most common ligases recruited are the von Hippel-Lindau (VHL) protein complex $CRL2^{VHL}$ and the cereblon (CRBN) complex $CRL4^{CRBN}$. Studies have shown that PROTACs made of the same target ligand but either VHL or CRBN ligands can exhibit different degradation selectivity and efficacy. In some systems, CRBN-based degraders show a more active profile than VHL-based molecules. These observations would suggest that the development of VHL and CRBN based degraders might require similar exploration in the PROTAC design than those based on any one of them specifically. Even if degradation of a given target protein can be readily obtained by recruiting one E3 ligase, emerging evidence suggests that it could be beneficial to develop a parallel chemical series hijacking other E3 ligases.

To design the library, based on our data of AZD5438-PROTAC 8, in the first set of PROTACS we will keep the VHL E3 ligase unaltered along with the CDK2 ligand (AZD5438), while we will only change the linker length as described in FIG. 1 (18 PROTACs are synthesized from the combination of E1, L1, L2, L3, L4). To restrict the rotation of the linker and increase the yield of the final product over mult-step, we will also use click chemistry approach to best fit the PROTAC with the proteins. We hypothesize that synthesized PROTACs after treatment of HEI-OC1 cells will provide us a clear idea about the structure activity relationships (SAR) because of the close similarity with the AZD5438-PROTAC 8 and able to degrade CDK2 completely. To achieve the selectivity, we will also synthesize the second set of the PROTACs, where we will modify the VHL ligand with the substitution on the nitrogen atom of the amine group as described in the E2 and the bond formation with the linker will take place with the aromatic group of the VHL ligand as described in FIG. 1. We aim to leverage available E3 ligase ligands and to maximize the opportunity for complementary surfaces between the CDK2 and the ligase within the ternary complex thus we will use different position of the E3 ligase recognition domain to connect with the linker. In the second set we expect to synthesize 24-30 PROTACs with click chemistry approach. Finally, we aim to use two different CRBN ligands (E3 and E4) with similar set of linkers with the help of optimized route to synthesize a parallel chemical series of PROTACs. Overall, we aim to build a library of 70-80 PROTACs to address the efficacy and selectivity toward CDK2 degradation.

In Vitro and In Vivo Efficacy Study of PROTACs

To elucidate the efficiency of the library, HEI-OC1 cells will be treated with different concentrations of the compounds starting from picomolar to micromolar range and perform the Western blot to see the degradation capacity of the molecules (CDK1/2/9). Due to the close similarity of the CDK family proteins, we will screen the compounds for the selectivity against CDK2 degradation. The top 10% molecules of the library will undergo further characterization ex vivo in cochlear explants, and in vivo in zebrafish lateral-line neuromasts. At this point in the study, we will be using an SPR-based assay to quantify the stability of the lead CDK2 specific PROTACs induced ternary complexes by measuring the kinetics of their formation and dissociation in vitro using purified proteins available from commercial sources. The SPR-based assay to quantitatively measure the kinetics of ternary complex formation and dissociation, which we will use to characterize the lifetime of ternary complexes composed of CDK2 protein, PROTACs, and E3 ligase. Using a Biacore SPR instrument and streptavidin immobilized biotin-VHL or CRBN, we will measure the kinetics and affinity of VHL or CRBN binding for a concentration series of either PROTAC alone (to form a binary complex) or PROTAC pre-incubated with near-saturating concentrations of CDK2 protein (to form a ternary complex with VHL or CRBN). Finally, we will test the best PROTAC from the library in FVB mice to assess selective degradation of CDK2 protein and compare its hearing ability with the CDK2 knockout mice upon cisplatin insult using auditory brainstem response (ABR) test. We will locally deliver the effective concentration of the PROTAC using transtympanic injection (TT) in the inner ear and isolate the cochlea to perform Western blot as we have done routinely in our lab.

Expected Outcomes

To synthesize the library of the PRTOAC, we have already optimized all the steps to get the final molecules with more than 37% yield. To reduce the chance of the lower yield, we will follow the library synthesis from a common intermediate. Based on our Western blot and zebrafish preliminary studies, we expect PROTACs will degrade CDK2 protein in FVB mice in vivo. Protection of hearing will be measured as ABR threshold shifts pre- and post-PROTAC treatment. We expect that at 14 day (D14) after treatment, threshold shifts from the PROTAC treatment groups will be similar to the CDK2 knockout mice, while those receiving vehicle will not be different from day one. If the given doses (TT) do not provide full degradation of CDK2 at D14, we will increase the injection concentration of the PROTAC to the maximum nontoxic dose.

Sample Size, Power Analysis, and Statistical Analysis

Our power analysis with an effect size of 0.5 at alpha=0.05 showed an estimated sample size of 10 mice per experimental condition for an effective power of 0.868 (G*Power). For Western blot analysis in zebrafish, we will use a sample size of 10 per condition. GraphPadPrism version 8 will be used for statistical analysis. ABR threshold shifts will be all analyzed with two-way analyses of variance (ANOVAs). Statistical significance will be set at P value $\leq 0.05$.

Sex as a Biological Variable

Both male and female zebrafish and FVB mice will be used in a roughly equal ratio per experimental group.

Scientific Rigor and Transparency

We will do randomization of the animals before the study. We will perform injection, hearing tests, and morphological analysis in a double-blinded manner, until all results are obtained.

OTHER EMBODIMENTS

It is to be understood that while the compounds and methods have been described in conjunction with the detailed description thereof, the foregoing description is intended to illustrate and not limit the scope, which is defined by the scope of the appended claims. Other aspects, advantages, and modifications are within the scope of the following claims.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound having the structure of Formula (1):

X-L-E    (1)

wherein X is a cyclin-dependent kinase 2 binding moiety;
L is a linking group selected from:
alkylene, (alkylene oxide)$_n$-alkylene, —C(=O)-alkylene, —C(=O)-alkylene-(alkylene oxide)$_n$-alkylene, —(C=O)-alkylene-O-alkylene, alkylene-(heteroaryl)-(alkylene oxide)$_m$-alkylene-C(=O)—, and alkylene-(heteroaryl)-(alkylene oxide)$_m$-alkylene;
wherein n and m are each independently an integer between 1 and 10; and
E is a ubiquitin ligase binding moiety, wherein X is selected from:

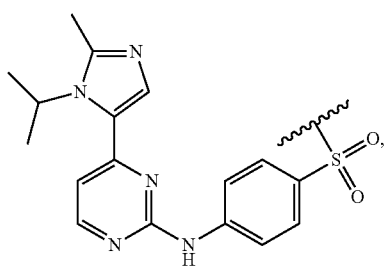

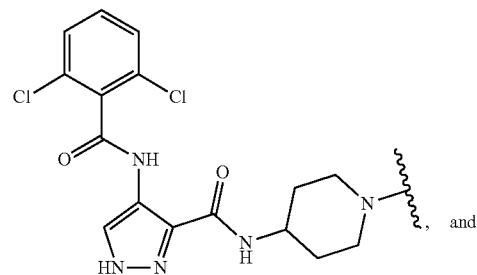

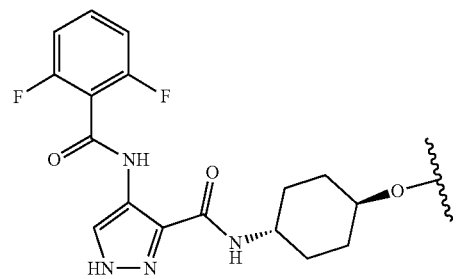

, wherein L is selected from:

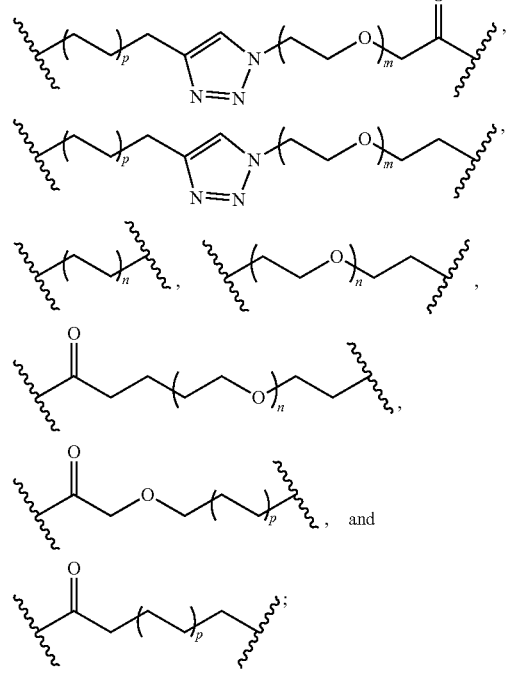

wherein n is an integer between 1 and 4, m is an integer between 2 and 4, and p is an integer between 0 and 4 and
, wherein E is selected from:

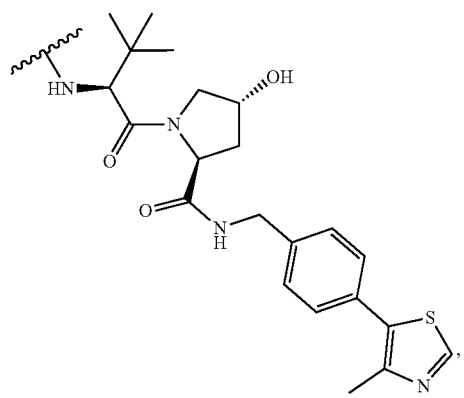

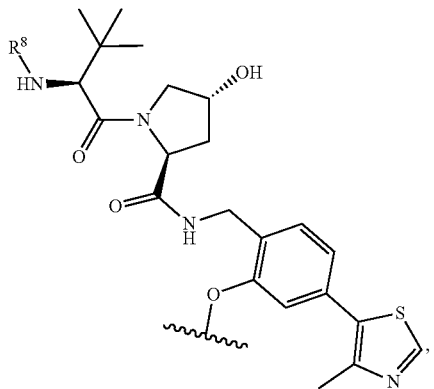

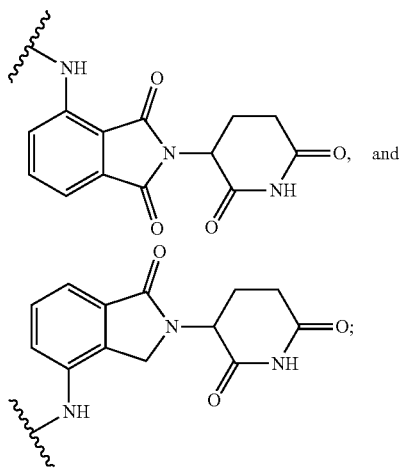

wherein R⁸ is selected from:

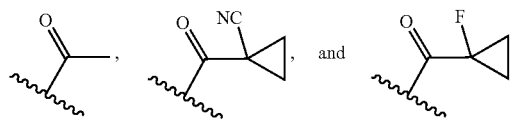

2. The compound of claim 1, wherein X is

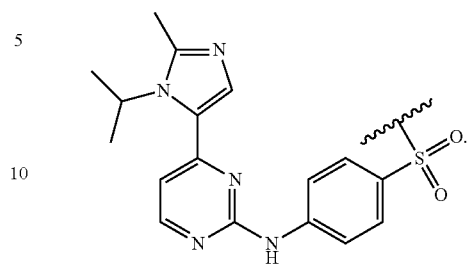

3. The compound of claim 1, wherein L is selected from:

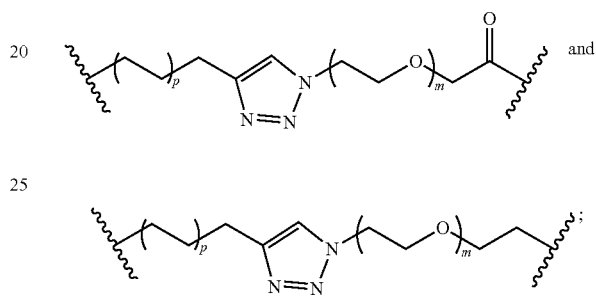

wherein p is 0, 1, 2, or 4, and
m is an integer between 2 and 4.

4. The compound of claim 1, wherein the ubiquitin ligase is Cereblon or von Hippel-Lindau.

5. The compound of claim 1, wherein the compound of Formula (1) is:

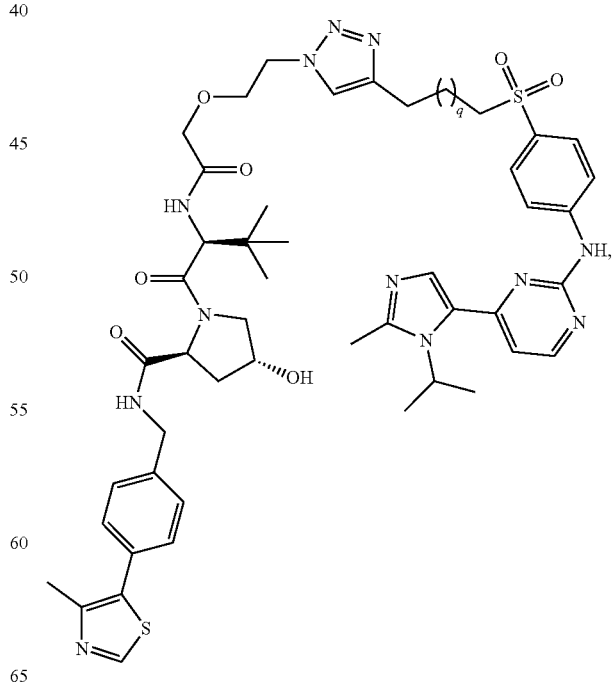

or a pharmaceutically acceptable salt thereof,

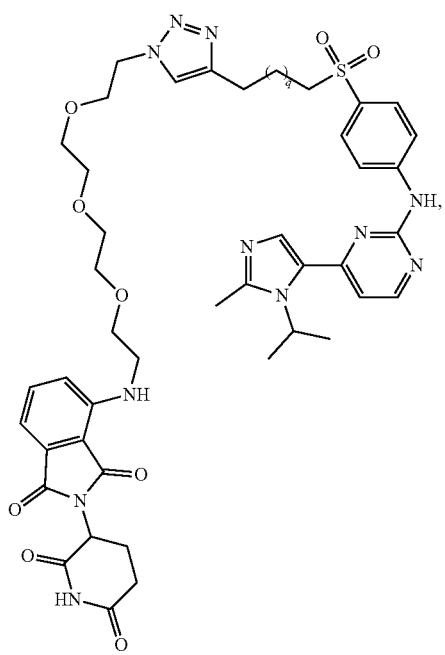

or a pharmaceutically acceptable salt thereof,

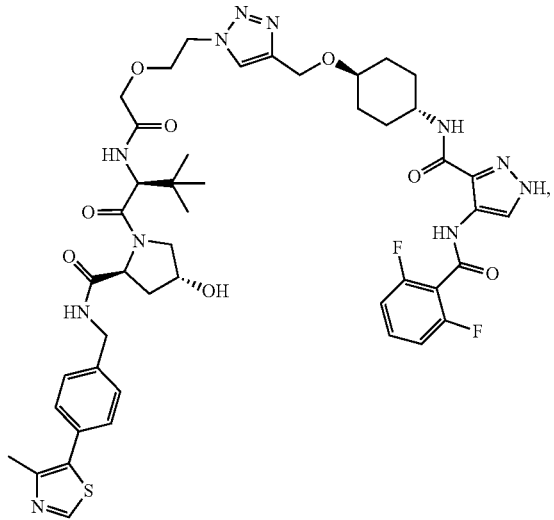 [SMILES: Cc1ncsc1-c1ccc(CNC(=O)[C@@H]2C[C@@H](O)CN2C(=O)[C@@H](NC(=O)COCCn2cc(CO[C@H]3CC[C@H](NC(=O)c4n[nH]cc4NC(=O)c4c(F)cccc4F)CC3)nn2)C(C)(C)C)cc1]

or a pharmaceutically acceptable salt thereof, or

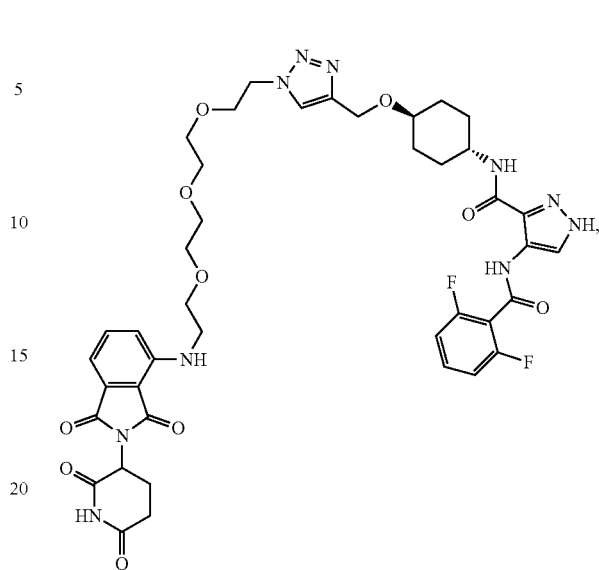

or a pharmaceutical salt thereof,
wherein q is 0 or 1.

6. The compound of claim 4, wherein the compound of Formula (1) is:

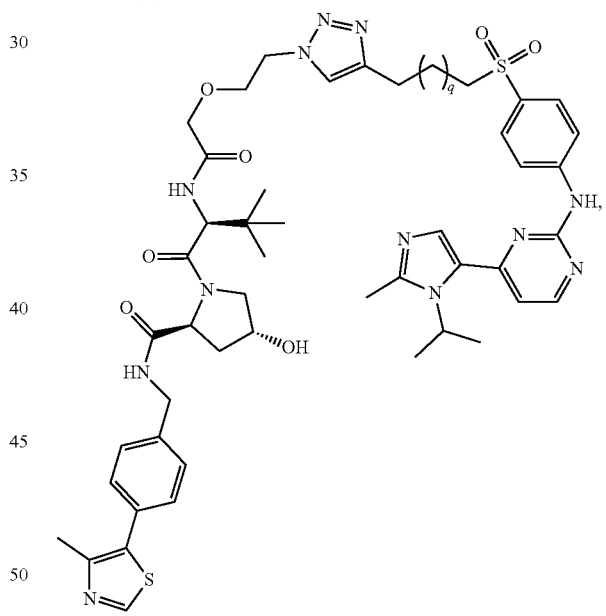

or a pharmaceutically acceptable salt thereof, wherein q is 1.

7. A pharmaceutical composition comprising a compound of claim 1, and a pharmaceutically acceptable carrier.

* * * * *